US010441541B2

(12) United States Patent
Cronstein et al.

(10) Patent No.: US 10,441,541 B2
(45) Date of Patent: Oct. 15, 2019

(54) METHODS AND COMPOSITIONS FOR TREATING OSTEOARTHRITIS AND PROMOTING CARTILAGE FORMATION

(71) Applicant: New York University, New York, NY (US)

(72) Inventors: Bruce N. Cronstein, New York, NY (US); Carmen Corciulo, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/262,372

(22) Filed: Sep. 12, 2016

(65) Prior Publication Data

US 2018/0036238 A1    Feb. 8, 2018

Related U.S. Application Data

(60) Provisional application No. 62/272,366, filed on Dec. 29, 2015, provisional application No. 62/218,173, filed on Sep. 14, 2015.

(51) Int. Cl.

| | | |
|---|---|---|
| *A61K 31/52* | (2006.01) | |
| *A61P 19/02* | (2006.01) | |
| *A61K 9/127* | (2006.01) | |
| *A61K 9/00* | (2006.01) | |
| *A61K 47/28* | (2006.01) | |
| *A61K 47/24* | (2006.01) | |
| *A61K 47/02* | (2006.01) | |
| *A61K 31/517* | (2006.01) | |
| *A61K 47/44* | (2017.01) | |
| *A61K 31/7076* | (2006.01) | |
| *A61K 31/53* | (2006.01) | |
| *A61K 31/519* | (2006.01) | |
| *A61K 31/522* | (2006.01) | |
| *A61K 47/10* | (2017.01) | |
| *A61K 45/06* | (2006.01) | |

(52) U.S. Cl.
CPC ............ *A61K 9/127* (2013.01); *A61K 9/0019* (2013.01); *A61K 31/517* (2013.01); *A61K 31/519* (2013.01); *A61K 31/52* (2013.01); *A61K 31/522* (2013.01); *A61K 31/53* (2013.01); *A61K 31/7076* (2013.01); *A61K 45/06* (2013.01); *A61K 47/02* (2013.01); *A61K 47/10* (2013.01); *A61K 47/24* (2013.01); *A61K 47/28* (2013.01); *A61K 47/44* (2013.01); *A61P 19/02* (2018.01)

(58) Field of Classification Search
None
See application file for complete search history.

(56) References Cited

U.S. PATENT DOCUMENTS

| | | | | |
|---|---|---|---|---|
| 5,932,558 | A  * | 8/1999 | Cronstein | .............. A61K 31/00 |
| | | | | 514/46 |
| 6,020,321 | A  * | 2/2000 | Cronstein | .............. A61K 31/00 |
| | | | | 514/46 |
| 8,183,225 | B2 * | 5/2012 | Cronstein | .......... A61K 31/7076 |
| | | | | 514/46 |
| 8,680,070 | B2 * | 3/2014 | Cronstein | .......... A61K 31/7076 |
| | | | | 514/45 |
| 15,591,653 | * | 5/2017 | Cronstein | .......... A61K 31/7076 |
| | | | | 514/262.1 |
| 2006/0241130 | A1* | 10/2006 | Keinan | ................... A61K 31/01 |
| | | | | 514/263.31 |
| 2007/0299043 | A1* | 12/2007 | Hunter | .................. A61F 2/0077 |
| | | | | 514/171 |
| 2008/0300213 | A1* | 12/2008 | Fishman | ................ A61K 31/00 |
| | | | | 514/46 |

(Continued)

FOREIGN PATENT DOCUMENTS

JP        2006-160628    *    6/2006    .......... C07D 487/04

OTHER PUBLICATIONS

English language abstract of Kato et al. JP2006-160628, from STN database CAPLUS (Year: 2006).*

(Continued)

*Primary Examiner* — Eric Olson
(74) *Attorney, Agent, or Firm* — Fisher Broyles LLP; J. David Smith

(57) ABSTRACT

The invention provides methods and compositions for treating or inhibiting the development of osteoarthritis in a subject having osteoarthritis or at risk for developing osteoarthritis and for stimulating or increasing cartilage production or formation in a subject. The methods feature administering to the subject a therapeutically effective amount of a composition comprising one or more agent from among adenosine, an adenosine receptor agonist, and an agent that upregulates or increases the amount of or the biological activity of adenosine, or an analog or derivative thereof. The adenosine receptor may be an $A_1$, $A_{2A}$, $A_{2B}$ and $A_3$ adenosine receptor. The agent that upregulates or increases the amount of or the biological activity of adenosine may be dipyridamole or ticagrelor. The composition may be administered via intraarticular injection such as injection into the synovial fluid of a joint. The composition may be effective to reduce or inhibit degeneration or damage to cartilage or to stimulate or increase cartilage production or formation. The composition may be a liposomal composition or contain a liposome.

32 Claims, 20 Drawing Sheets

Specification includes a Sequence Listing.

(56) References Cited

U.S. PATENT DOCUMENTS

2012/0283211 A1* 11/2012 Cronstein .......... A61K 31/7076
514/45

OTHER PUBLICATIONS

English machine translation of JP2006-160628, downloaded from espacenet.com (Year: 2006).*

Ferrari et al., "Purinergic Signalling in Scarring" FASEB Journal vol. 30 pp. 3-12 (Year: 2016).*

Hung et al., "Dipyridamole inhibits human peritoneal mesothelial cell proliferation in vitro and attenuates rat peritoneal fibrosis in vivo" Kidney International vol. 59 pp. 2316-2324 (Year: 2001).*

Kvien et al., "Efficacy and safety of a novel synergistic drug candidate, CRx-102, in hand osteoarthritis" Annals of Rheumatic Disease vol. 67 pp. 942-948 (Year: 2008).*

Butoescu et al., "Intra-articular drug delivery systems for the treatment of rheumatic diseases: A review of the factors influencing their performance" European Journal of Pharmaceutics and Biopharmaceutics vol. 73 pp. 205-218 (Year: 2009).*

Ozkan et al., "Intra-articular hyaluronate, tenoxicam and vitamin E in a rat model of osteoarthritis: evaluation and comparison of chondroprotective efficacy" Int J CLin Exp Med vol. 8 No. 1 pp. 1018-1026 (Year: 2015).*

Park et al., "Linnonene, a natural cyclic terpene, is an agonistic ligand for adenosine A2A receptors" Biochemical and Biophysical Research Communications vol. 404 pp. 345-348 (Year: 2011).*

Cohen et al., "Reducing joint destruction due to septic arthrosis using an adenosine2A receptor agonist" Journal of Orthopaedic Research vol. 22 pp. 427-435 (Year: 2004).*

* cited by examiner

Uninvolved and Osteoarthritic Knees
Treated with Saline or Adenosine Liposomal Suspensions Control OA + Saline Liposomes OA + Adenosine Liposomes MicroCTs of Uninvolved and Osteoarthritic Knees
Treated with Saline or Adenosine Liposomal Suspensions Control OA + Saline Liposomes OA + Adenosine Liposomes

FIG. 3A
Uninvolved knee
FEMUR
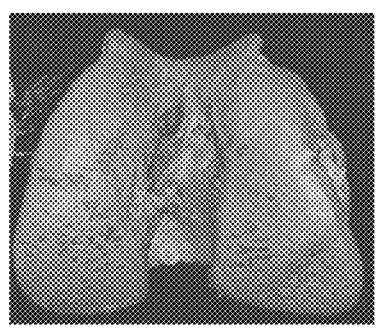
TIBIA
FIG. 3B
Saline
FEMUR
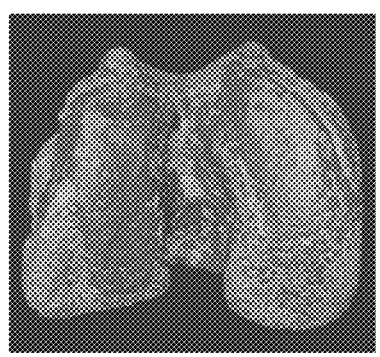
TIBIA
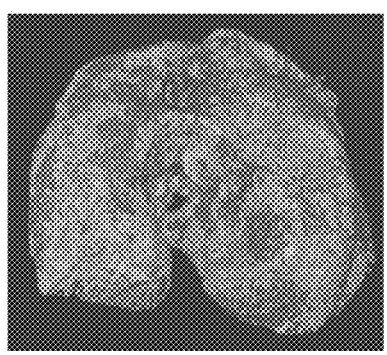

FIG. 3C
Liposome
FEMUR
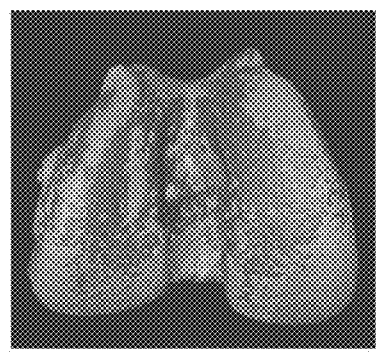
TIBIA
FIG. 3D
Liposome+
CGS21680
FEMUR
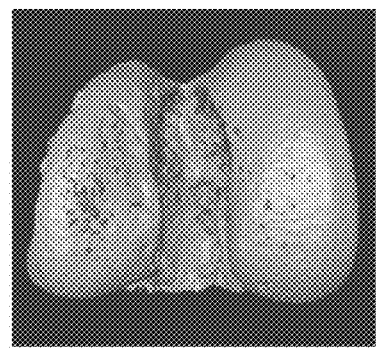
TIBIA
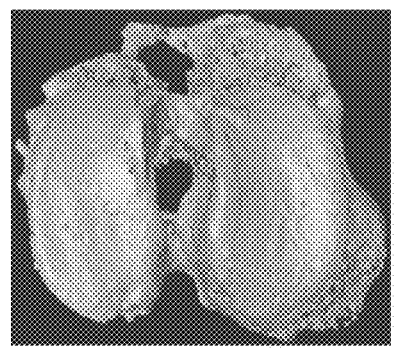

ALCIAN BLUE STAINING FOR AGGREGAN DETECTION

7 DAYS TREATMENT

FIG. 4C

CGS treated rats

Cartilage volume (% vs uninvolved knee)

|  | Femur | Tibia |
|---|---|---|
| Rat 1 (05 L1)) | 155% | 160% |
| Rat 2 (03 L1) | 465% | 100% |
| Rat 3 (03 L0) | 152% | 59% |

Basal value

Medial tibia plateau 15 min loading-Medial tibia plateau

FIG. 9A
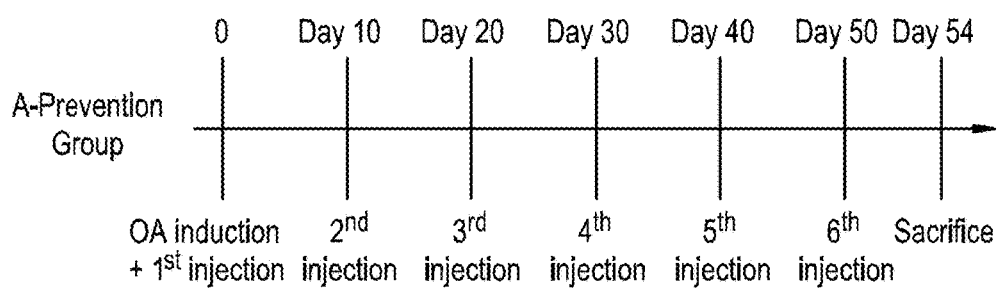
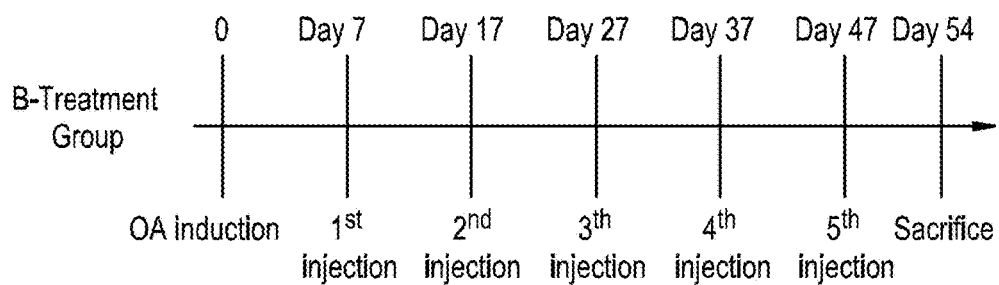

Prevention Group

Treatment Group

Prevention Group

Treatment Group

WT

A2ARKO

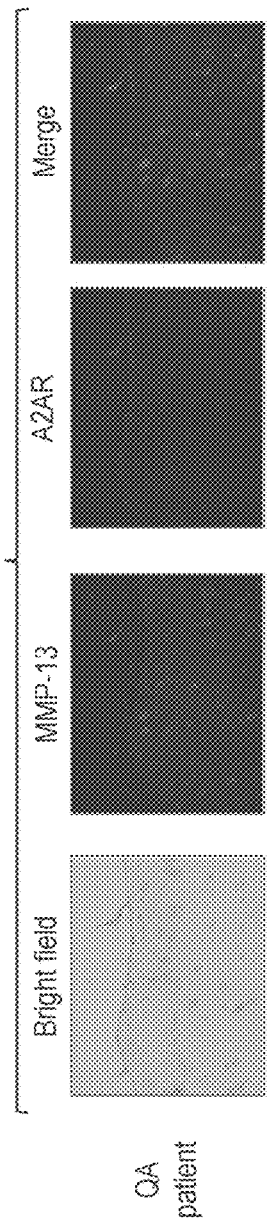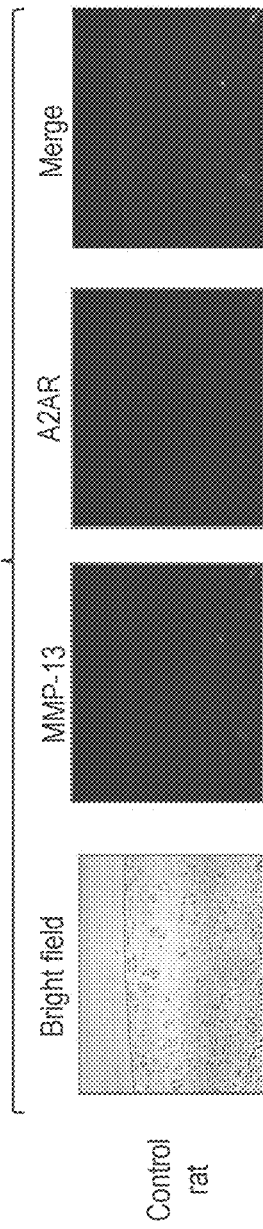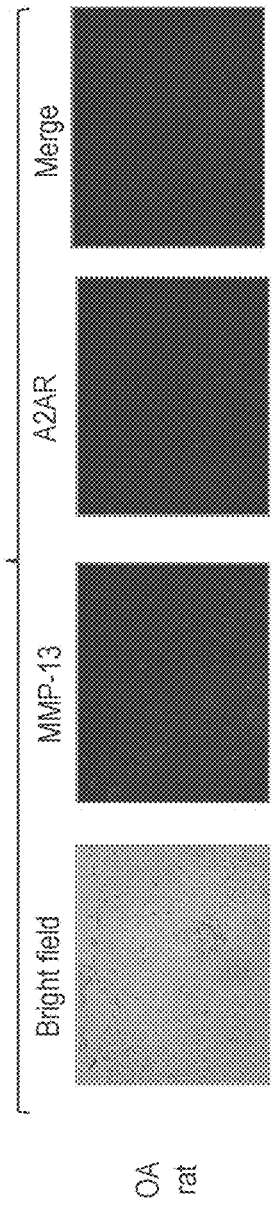

24 hours IL-1β treatment (5ng/ml)

OA Control

METHODS AND COMPOSITIONS FOR TREATING OSTEOARTHRITIS AND PROMOTING CARTILAGE FORMATION

FIELD OF THE INVENTION

The present invention relates to methods and compositions for inhibiting and treating osteoarthritis and for promoting cartilage formation, particularly liposomes and liposomal compositions containing an adenosine receptor agonist, or an analog or derivative thereof or a therapeutically effective amount of adenosine or a therapeutically effective amount of an agent that upregulates, increases the amount of or the biological activity of adenosine.

BACKGROUND OF THE INVENTION

Adenosine is a nucleoside that occurs naturally in mammals, which acts as a ubiquitous biochemical messenger. The heart, for instance, produces and releases adenosine in order to modulate heart rate and coronary vasodilation. Likewise, adenosine is produced in the kidney to modulate essential physiological responses, including glomerular filtration rate (GFR), electrolyte reabsorption, and renin secretion.

Adenosine is known to bind to and activate seven-transmembrane spanning G-protein coupled receptors, thereby eliciting a variety of physiological responses. There are 4 known subtypes of adenosine receptors (i.e., $A_1$, $A_{2A}$, $A_{2B}$, and $A_3$), which mediate different, and sometimes opposing, effects. For example, activation of the adenosine $A_1$ receptor, elicits an increase in renal vascular resistance, which leads to a decrease in glomerular filtration rate (GFR), while activation of the adenosine $A_{2A}$ receptor elicits a decrease in renal vascular resistance. Conversely, blockade of the $A_1$ adenosine receptor decreases afferent arteriole pressure, leading to an increase in GFR and urine flow, and sodium excretion. Furthermore, $A_{2A}$ adenosine receptors modulate coronary vasodilation, whereas $A_{2B}$ receptors have been implicated in mast cell activation, asthma, vasodilation, regulation of cell growth, intestinal function, and modulation of neurosecretion (See, Adenosine $A_{2B}$ Receptors as Therapeutic Targets, *Drug Dev Res* 45:198; Feoktistov et al., *Trends Pharmacol Sci* 19:148-153 and Ralevic, V and Burnstock, G. (1998), Pharmacological Reviews, Vol. 50: 413-492), and $A_3$ adenosine receptors modulate cell proliferation processes. Two receptor subtypes ($A_1$ and $A_{2A}$) exhibit affinity for adenosine in the nanomolar range while two other known subtypes $A_{2B}$ and $A_3$ are low-affinity receptors, with affinity for adenosine in the low-micromolar range. $A_1$ and $A_3$ adenosine receptor activation can lead to an inhibition of adenylate cyclase activity, while $A_{2A}$ and $A_{2B}$ activation causes a stimulation of adenylate cyclase.

It has been shown that adenosine, acting at specific cell surface receptors, has the potential to suppress inflammation and that inflammation itself may increase extracellular adenosine levels (Cronstein, et al., 1986, *Journal of Clinical Investigation* 78:760-770; Cronstein, et al., 1983, *Journal of Experimental Medicine* 158:1160-1177). Further, it has been demonstrated that adenosine mediates the anti-inflammatory effects of low-dose methotrexate therapy for Rheumatoid Arthritis (Reviewed in Cronstein, 2005, *Pharmacol Rev* 57:163-172). Exploration of the therapeutic and toxic properties of methotrexate in the treatment of RA has led to a number of other potentially important pre-clinical therapeutic developments. Methotrexate increases giant cell formation from peripheral blood monocytes and that this effect is mediated by adenosine acting at $A_1$ receptors (Merrill, et al., *Arth. Rheum.* 40:1308-1315). In addition, $A_{2A}$ receptor antagonists promote giant cell formation by diminishing the effect of endogenous adenosine although the $A_1$ receptor-mediated promotion of giant cell formation appears to dominate.

Cronstein, U.S. Pat. No. 7,795,427 describes the use of agents that block adenosine $A_1$ receptor antagonists to diminish osteoclast function and thereby prevent the development of osteoporosis. U.S. Pat. No. 8,183,225 describes the activation of adenosine $A_{2A}$ receptors as inhibiting osteoclast formation and function, and use of adenosine $A_{2A}$ receptor agonists to prevent wear particle-induced bone resorption. In all of these actions adenosine receptor blockade or activation was directed solely at preventing bone resorption. Interestingly, these studies do not demonstrate that either adenosine $A_1$ or $A_{2A}$ receptors affect the formation or function of osteoblasts. U.S. Ser. No. 14/380,238 describes the use of modulators of an adenosine receptor, including agonists of an adenosine $A_{2A}$ receptor and antagonists of an $A_1$ receptor, to stimulate bone regeneration and stimulate and promote differentiation and activation of osteoblasts as well as potentially inhibit bone resorption and inhibit differentiation and stimulation of osteoclasts.

The prior art also teaches use of adenosine receptor agonists and antagonists or dipyridamole in the regulation of osteoblast differentiation, proliferation and function. Moreover, any proposed use of dipyridamole described in the prior art is to increase adenosine to stimulate adenosine $A_{2B}$ receptors to stimulate osteoblast production of bone matrix and inhibit IL-6 production or increase production of osteoprotegerin. (See, e.g., Kara et al., *The FASEB Journal* 2010; 24:2325-2333; Kara et al., *Arthritis and Rheumatism* 2010; 62:534-541; Russell et al., *Calcif Tissue Int* 2007; 81:316-326; Evans et al., *J Bone Miner Res* 2006; 21:228-236; Costa et al., *Journal of Cellular Physiology* 2011; 226:1353-1366).

Adenosine is an endogenously produced physiologic regulator whose intracellular and extracellular concentration is tightly regulated by oxygen consumption, cellular stress and mitochondrial functionality. Extracellular adenosine derives mainly from hydrolysis of ATP (primarily, but not exclusively, by the ectoenzymes CD39 and CD73) and mediates its effects via activation of G protein coupled receptors (A1R, A2AR, A2BR, A3R). Adenosine has long been known to regulate inflammation and immune responses (Hasko et al., *Nature Reviews. Drug Discovery* 2008; 7:759-770; Hasko et al., *Frontiers in Immunology* 2013; 4:85), and recent work has demonstrated the importance of adenosine and its receptors in osteoblast, osteoclast, and bone marrow homeostasis (Kara et al., *FASEB Journal: official publication of the Federation of American Societies for Experimental Biology* 2010; 24:2325-2333; Kara et al., *Arthritis and Rheumatism* 2010; 62:31534-541; He et al., *Front Biosci* (Elite Ed) 2011; 3:888-895; He et al., *Purinergic Signalling* 2012; 8:327-337; Mediero et al., *Am J Pathol* 2012; 180: 775-786; He et al., *FASEB Journal: official publication of the Federation of American Societies for Experimental Biology* 2013; 27:3446-3454; He et al., *British Journal of Pharmacology* 2013; 170:1167-1176; Mediero et al., *Trends in endocrinology and metabolism: TEM* 2013; 24:290-300; Mediero et al., *British Journal of Pharmacology* 2013; 169:1372-1388; Lerner et al., *Acta Physiol Scand* 1987; 131:287-296; Shimegi et al., *Calcified Tissue International* 1996; 58:109-113; Jones et al., *Bone* 1997; 21:393-399; Shimegi et al., *Calcified Tissue International* 1998; 62:418-425; Evans et al., *Journal of Bone and Mineral Research: the official journal of the American Society for Bone and*

Mineral Research 2006; 21: 228-236; Russell et al., *Calcified tissue international* 2007; 81:316-326; Orriss et al., *Current opinion in pharmacology* 2010; 10:322-330; Costa et al., *Journal of cellular physiology* 2011; 226:1353-1366; Gartland et al. *Front Biosci (Landmark Ed)* 2012; 17:16-29). Prior studies have suggested that adenosine receptors also regulate chondrocyte physiology and pathology in response to inflammatory stimuli although the specific receptor(s) involved have not been fully clarified. Removal of endogenous adenosine (by addition of adenosine deaminase) or blockade of A2AR leads to cartilage degradation in equine cartilage explants although equine purine metabolism differs from other species as adenosine deaminase, present in lymphocytes, plasma and extracellular fluid of most species, is not present in horse lymphocytes or serum (Koolpe et al., *Arthritis and rheumatism* 1999; 42:258-267; Benton et al., *Am J Vet Res* 2002; 63:204-210; Tesch et al., *Osteoarthritis and cartilage/OARS, Osteoarthritis Research Society* 2002; 10:34-43; Kono et al., *Cell Biochem Funct* 2006; 24:103-111; Varani et al., *Osteoarthritis and Cartilage/OARS, Osteoarthritis Research Society* 2008; 16:292-304; Tesch et al., *Osteoarthritis and Cartilage/OARS, Osteoarthritis Research Society* 2004; 12:349-359; Hovi et al., *Clinical and Experimental Immunology* 1976; 23:395-403; Tax et al., *Comp Biochem Physiol B* 1978; 61:439-441). More recently A3R stimulation was reported to diminish OA development in a chemically induced model of OA35, principally due to the anti-inflammatory effects of A3R agonists.

Mice lacking A2AR were first developed by Chen and colleagues in 1999 and, in general, these mice have few obvious defects (Chen et al., *J Neurosci* 1999; 19:9192-9200). Interestingly, they do suffer osteopenia as a result of an increase in osteoclast number and function and they respond abnormally to a variety of stressors reflecting the loss of the A2AR. However, as these mice age they have increasing difficulty in grabbing food, walking, and mating, and the diminished mobility of A2AR-deficient mice might be due to intrinsic joint disease.

Osteoarthritis (OA) is the most common type of arthritis, affecting up to 25% of the 3 population over 65, and 12% of all cases may be due to prior joint trauma (Lieberthal et al., *Osteoarthritis and cartilage/OARS, Osteoarthritis Research Society* 2015; 23:1825-1834; Brown et al., *Journal of Orthopaedic Trauma* 2006; 20:739-744). Worldwide in its distribution, the incidence of OA increases with age and the resulting pain, loss of joint function and mobility, social isolation, and a broadly reduced quality of life make OA a condition with a high medical and social impact. Current treatment options are less than optimal and do not correct the underlying problem with the result that joint replacement surgery is often the eventual outcome (Mobasheri et al., *Current Rheumatology Reports* 2013; 15:364).

OA is characterized by changes in every structure in the joint, including cartilage destruction, synovial inflammation, osteophyte formation, enthesophytes, and significant bony changes (Wieland et al., *Nature Reviews. Drug Discovery* 2005; 4:331-344). The central player in OA is the chondrocyte, which responds to excess mechanical loading by releasing inflammatory mediators and proteolytic enzymes causing further cartilage damages. In addition, age-related inflammation contributes to the pathogenesis of OA (Loeser et al., *Nature Reviews. Rheumatology* 2016; 12:412-420).

Liposomes are spherical vesicles having at least one lipid bilayer. The liposome can be used as a vehicle for administration of nutrients and pharmaceutical drugs. Liposomes can be prepared by disrupting biological membranes (such as by sonication). Liposomes are most often composed of phospholipids, especially phosphatidylcholine, but may also include other lipids, such as egg phosphatidylethanolamine, so long as they are compatible with lipid bilayer structure. Cevc, *Journal of Controlled Release,* 1993; 160 (2): 135-146 A liposome design may employ surface ligands for attaching to unhealthy tissue. Torchilin, *Advanced Drug Delivery Reviews* 2006; 58 (14): 1532-55.

The major types of liposomes are the multilamellar vesicle (MLV, with several lamellar phase lipid bilayers), the small unilamellar liposome vesicle (SUV, with one lipid bilayer), the large unilamellar vesicle (LUV), and the cochleate vesicle. A less desirable form are multivesicular liposomes in which one vesicle contains one or more smaller vesicles.

A liposome has an aqueous solution core surrounded by a hydrophobic membrane, in the form of a lipid bilayer; hydrophilic solutes dissolved in the core cannot readily pass through the bilayer. Hydrophobic chemicals associate with the bilayer. A liposome can be hence loaded with hydrophobic and/or and hydrophilic molecules. To deliver the molecules to a site of action, the lipid bilayer can fuse with other bilayers such as the cell membrane, thus delivering the liposome contents; this is a complex and non-spontaneous event, however. Cevc, *Advanced Drug Delivery Reviews,* 1993; 38 (3): 207-232 By preparing liposomes in a solution of DNA or drugs (which would normally be unable to diffuse through the membrane) they can be (indiscriminately) delivered past the lipid bilayer, but are then typically distributed non-homogeneously. Barenholz, et al., (2000). Physical chemistry of biological surfaces, Chapter 7: Structure and properties of membranes. New York: Marcel Dekker. pp. 171-241.

Liposomes are used as models for artificial cells. Liposomes can also be designed to deliver drugs in other ways. Liposomes that contain low (or high) pH can be constructed such that dissolved aqueous drugs will be charged in solution (i.e., the pH is outside the drug's pI range). As the pH naturally neutralizes within the liposome (protons can pass through some membranes), the drug will also be neutralized, allowing it to freely pass through a membrane. These liposomes work to deliver drug by diffusion rather than by direct cell fusion.

A similar approach can be exploited in the biodetoxification of drugs by injecting empty liposomes with a transmembrane pH gradient. In this case the vesicles act as sinks to scavenge the drug in the blood circulation and prevent its toxic effect. Bertrand, et al., *ACS Nano* 4 2000; (12): 7552-8 Another strategy for liposome drug delivery is to target endocytosis events. Liposomes can be made in a particular size range that makes them viable targets for natural macrophage phagocytosis. These liposomes may be digested while in the macrophage's phagosome, thus releasing its drug. Liposomes can also be decorated with opsonins and ligands to activate endocytosis in other cell types. The use of liposomes for transformation or transfection of DNA into a host cell is known as lipofection.

As of 2012, some 13 drugs with liposomal delivery systems have been approved and five additional liposomal drugs were in clinical trials. The clinically approved liposomal drugs include amphotericin B, ctyarabine, daunorubicin, doxorubicin, IRIV vaccine, morphine, verteporfin, proteins SP-B and SP-C, estradiol, vincristine, and PEG.

Liposomes rarely form spontaneously. They typically form after supplying enough energy to a dispersion of (phospho)lipids in a polar solvent, such as water, to break down multilamellar aggregates into oligo- or unilamellar bilayer vesicles. Cevc, *Journal of Controlled Release,* 1993;

160 (2): 135-146; Barenholz, et al., (2000). Physical chemistry of biological surfaces, Chapter 7: Structure and properties of membranes. New York: Marcel Dekker. pp. 171-241.

Liposomes can hence be created by sonicating a dispersion of amphipatic lipids, such as phospholipids, in water. Low shear rates create multilamellar liposomes. The original aggregates, which have many layers like an onion, thereby form progressively smaller and finally unilamellar liposomes (which are often unstable, owing to their small size and the sonication-created defects). Sonication is generally considered a "gross" method of preparation as it can damage the structure of the drug to be encapsulated. Newer methods such as extrusion and Mozafari method are employed to produce materials for human use. Colas, et al., "Microscopical investigations of nisin-loaded nanoliposomes prepared by Mozafari method and their bacterial targeting". Micron (Oxford, England: 1993) 2007; 38 (8): 841-7 Using lipids other than phosphatidylcholine can greatly facilitate liposome preparation. Cevc, *Journal of Controlled Release*, 1993; 160 (2): 135-146.

All publications, patent applications, patents and other reference material mentioned are incorporated by reference in their entirety. In addition, the materials, methods and examples are only illustrative and are not intended to be limiting. The citation of references herein is not to be construed as an admission that the references are prior art to the present invention.

SUMMARY OF THE INVENTION

In a first aspect, the invention provides a method for treating or inhibiting the development of osteoarthritis in a subject having osteoarthritis or at risk for developing osteoarthritis, featuring administering to the subject a therapeutically effective amount of a composition containing one or more agent from among adenosine, an adenosine receptor agonist, and an agent that upregulates or increases the amount of or the biological activity of adenosine, or an analog or derivative thereof. The composition may be in a form useful to extend the life of the adenosine, the adenosine receptor agonist, or the agent that upregulates or increases the amount of or the biological activity of the adenosine, or an analog or derivative thereof. The composition may prolong drug release or may protect the adenosine, the adenosine receptor agonist, or the agent that upregulates or increases the amount of or the biological activity of the adenosine, or an analog or derivative thereof, from degradation. In some instances, the composition may contain a liposome or liposomal composition, a hyaluronate suspension, a microsphere, a nanofiber, a protein conjugate, or a nanoparticle. In some particular instances, the composition contains liposomes or is a liposomal composition.

The adenosine receptor may be an $A_1$, $A_{2A}$, $A_{2B}$ or $A_3$ adenosine receptor. The adenosine receptor agonist may be, for instance, an adenosine receptor $A_{2A}$ agonist, and the adenosine receptor agonist may be a selective adenosine receptor agonist. The agent that upregulates or increases the amount of or the biological activity of adenosine may be dipyridamole or ticagrelor.

The method may further feature administering one or more other therapeutically effective compound or agent. The one or more other therapeutically effective compound or agent may be, for instance, an anti-inflammatory compound, a bisphosphonate or a growth factor.

The composition, such as a liposome or liposomal composition, may be administered via intraarticular injection, and it may be injected into the synovial fluid of a joint. Likewise, the composition may be effective to reduce or inhibit degeneration or damage to cartilage. The composition and the one or more other therapeutically effective compound or agent may be administered concurrently or sequentially.

In a second aspect, the invention provides a method for stimulating or increasing cartilage production or formation in a subject featuring administering to the subject a therapeutically effective amount of a composition containing one or more agent from among adenosine, an adenosine receptor agonist, and an agent that upregulates or increases the amount of or the biological activity of adenosine, or an analog or derivative thereof. The subject may have osteoarthritis or be at risk for developing osteoarthritis. The composition may be in a form useful to extend the life of the adenosine, the adenosine receptor agonist, or the agent that upregulates or increases the amount of or the biological activity of the adenosine, or an analog or derivative thereof. The composition may prolong drug release or may protect the adenosine, the adenosine receptor agonist, or the agent that upregulates or increases the amount of or the biological activity of the adenosine, or an analog or derivative thereof, from degradation. In some instances, the composition may contain a liposome or liposomal composition, a hyaluronate suspension, a microsphere, a nanofiber, a protein conjugate, or a nanoparticle. In some particular instances, the composition contains liposomes or is a liposomal composition.

The adenosine receptor may be an $A_1$, $A_{2A}$, $A_{2B}$ or $A_3$ adenosine receptor. The adenosine receptor agonist may be, for instance, an adenosine receptor $A_{2A}$ agonist, and the adenosine receptor agonist may be a selective adenosine receptor agonist. The agent that upregulates or increases the amount of or the biological activity of adenosine may be dipyridamole or ticagrelor.

The method may further feature administering one or more other therapeutically effective compound or agent. The one or more other therapeutically effective compound or agent may be, for instance, an anti-inflammatory compound, a bisphosphonate or a growth factor.

The composition, such as a liposome or liposomal composition, may be administered via intraarticular injection, and it may be injected into the synovial fluid of a joint. Likewise, the liposome or liposomal composition may be effective to stimulate or increase cartilage production or formation. The composition and the one or more other therapeutically effective compound or agent may be administered concurrently or sequentially.

In a third aspect, the invention provides a composition containing a therapeutically effective amount of one or more of adenosine, an adenosine receptor agonist, or an agent that upregulates or increases the amount of or the biological activity of adenosine, or an analog or derivative thereof. The adenosine receptor may be an $A_1$, $A_{2A}$, $A_{2B}$ and $A_3$ adenosine receptor. The adenosine receptor agonist may be, for instance, an adenosine receptor $A_{2A}$ agonist, and the adenosine receptor agonist may be a selective adenosine receptor agonist. The agent that upregulates or increases the amount of or the biological activity of adenosine may be dipyridamole or ticagrelor. The composition may be in a form useful to extend the life of the adenosine, the adenosine receptor agonist, or the agent that upregulates or increases the amount of or the biological activity of the adenosine, or an analog or derivative thereof. The composition may prolong drug release or may protect the adenosine, the adenosine receptor agonist, or the agent that upregulates or increases the amount of or the biological activity of the adenosine, or an analog or derivative thereof, from degradation. In some instances, the composition may contain a liposome or liposomal composition, a hyaluronate suspension, a microsphere, a nanofiber, a protein conjugate, or a nanoparticles. In some particular instances, the composition contains liposomes or is a liposomal composition.

The composition may further contain one or more other therapeutically effective compound or agent. The one or more other therapeutically effective compound or agent may be an anti-inflammatory compound, a bisphosphonate or a growth factor.

The composition, such as a liposome or liposomal composition, may be suitable for intraarticular injection. Further, the composition may be suitable for injection into the synovial fluid of a joint. Likewise, the composition may be effective to reduce or inhibit degeneration or damage to cartilage or to stimulate or increase cartilage production or formation in a subject.

For each of these aspects, the adenosine receptor agonist may affect more than one adenosine receptor. Similarly, the adenosine receptor agonist may be a selective adenosine receptor agonist or may be a non-selective adenosine receptor agonist. In a more particular embodiment, the agent that agonizes an adenosine receptor may be an adenosine $A_{2A}$ receptor agonist or an adenosine $A_{2B}$ receptor agonist. The adenosine receptor agonist may be, for instance, a small organic molecule, a protein or peptide, a nucleic acid or an antibody.

In some more particular embodiments, the adenosine receptor agonist may be capable of substantially stimulating the endogenous activity of the adenosine receptor substantially the same as though the adenosine receptor had encountered its natural, endogenous ligand. Adenosine $A_{2A}$ receptor agonists are well known in the art. Many are disclosed in, for instance, U.S. Pat. Nos. 7,226,913 and 6,326,359 and in United States Patent Publication Nos. 20070225247, 20060100169, 20060034941, 20050261236, 20050182018, 20050171050, 20050020915 and 20040064039, the disclosures of which are herein incorporated by reference in their entireties. In another more particular embodiment, the adenosine $A_{2A}$ receptor agonist may be CGS 21680, MRE-0094, IB-MECA, R-PIA, binodenoson, or ATL146. Adenosine $A_{2B}$ receptor agonists are also known in the art. Many are disclosed in, for instance, United States Patent Publication Nos. 20070225335 and 20070240433.

Other objects and advantages will become apparent to those skilled in the art from a review of the following description and with reference to the following illustrative figures.

BRIEF DESCRIPTION OF THE FIGURES

FIG. 3(A,B,C,D) provides representative microCTs of the femur and tibia from a control knee and an arthritic knee treated with either saline, liposomes alone or liposomes containing an adenosine $A_{2A}$ receptor agonist, in this case CGS21680. The smooth surface of the cartilage in the control knee (FIG. 3A) and the osteoarthritis knee treated with liposomes containing an adenosine $A_{2A}$ receptor agonist, in this case CGS21680 (FIG. 3D) is apparent. Destructive changes are apparent in the bones of the osteoarthritis knees treated with saline (FIG. 3B) or liposomes alone (FIG. 3C) in contrast to the bones treated with liposomes containing the adenosine $A_{2A}$ receptor agonist, in this case CGS21680 (FIG. 3D).

FIG. 6(A,B,C,D,E) represents expression and release of osteoarthritis markers in primary chondrocytes from A2AR-KO and WT mice.

FIG. 11(A,B,C) demonstrates that A2AR is highly expressed in OA cartilage. Tissue sections from paraffin-embedded blocks of decalcified bone obtained from post-traumatic OA rats (FIGS. 11 B and C) and from an OA patient (FIG. 11A) at the time of joint replacement were obtained from the NYU Biorepository (top row) and immunologic staining for MMP13 and A2AR carried out, as described in Example 5. Representative fields (original magnification 400× for human samples and 200× for rat samples) are shown.

DETAILED DESCRIPTION OF THE INVENTION

Figure 1A:
FIG. 1(A,B,C) provides representative photographs of femoral condyles from a control knee and a knee treated with either liposomes containing saline or liposomes containing adenosine. The smooth surface of the cartilage in the control knee (FIG. 1A) and the osteoarthritis knee treated with adenosine-containing liposomes (FIG. 1C) is apparent. Similarly, representative microCT images of uninvolved (control) and saline-containing or adenosine-containing liposomes demonstrate the same. Destructive changes are apparent in the bone of the osteoarthritis knee treated with saline-containing liposomes (FIG. 1B) in contrast to the condyles treated with the adenosine containing liposomes.

Before the present methods and treatment methodology are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

By "agonist" is meant a substance that binds to a specific receptor and triggers a response in a cell. It mimics the action of an endogenous ligand (such as hormone or neurotransmitter) that binds to the same receptor. A "full agonist" binds (has affinity for) and activates a receptor, displaying full efficacy at that receptor. One example of a drug that acts as a full agonist is isoproterenol which mimics the action of acetylcholine at β adrenoreceptors. A "partial agonist" (such as buspirone, aripiprazole, buprenorphine, or norclozapine) also binds and activates a given receptor, but has only partial efficacy at the receptor relative to a full agonist. A "partial agonist" may also be considered a ligand that displays both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. A "co-agonist" works with other co-agonists to produce the desired effect together. An antagonist blocks a receptor from activation by agonists. Receptors can be activated or inactivated either by endogenous (such as hormones and neurotransmitters) or exogenous (such as drugs) agonists and antagonists, resulting in stimulating or inhibiting a biological response. A ligand can concurrently behave as agonist and antagonist at the same receptor, depending on effector pathways.

The potency of an agonist is usually defined by its $EC_{50}$ value. This can be calculated for a given agonist by determining the concentration of agonist needed to elicit half of the maximum biological response of the agonist. Elucidating an $EC_{50}$ value is useful for comparing the potency of drugs with similar efficacies producing physiologically similar effects. The lower the $EC_{50}$, the greater the potency of the agonist and the lower the concentration of drug that is required to elicit a maximum biological response.

"Antagonist" refers to an agent that down-regulates (e.g., suppresses or inhibits) at least one bioactivity of a protein. An "antagonist" or an agent that "antagonizes" may be a compound which inhibits or decreases the interaction between a protein and another molecule, e.g., a target peptide or enzyme substrate. An antagonist may also be a compound that down-regulates expression of a gene or which reduces the amount of expressed protein present. Methods for assessing the ability of an agent to "antagonize" or "inhibit" an adenosine receptor are known to those skilled in the art.

"Analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention (e.g. to treat or prevent bone disease, or to modulate osteoclast differentiation), but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

A "small molecule" refers to a molecule that has a molecular weight of less than 3 kilodaltons (kDa), preferably less than about 1.5 kilodaltons, more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is normally an organic compound (or organic compound complexed with an inorganic compound (e.g., metal)) that has a molecular weight of less than 3 kilodaltons, and preferably less than 1.5 kilodaltons, and more preferably less than about 1 kDa.

"Diagnosis" or "screening" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or one of the compounds may be administered first, followed by the second agent, e.g. sequentially. The desired result can be either a subjective relief of one or more symptoms or an objectively identifiable improvement in the recipient of the dosage.

"Modulation" or "modulates" or "modulating" refers to up regulation (i.e., activation or stimulation), down regulation (i.e., inhibition or suppression) of a response, or the two in combination or apart.

As used herein, the term "candidate compound" or "test compound" or "agent" or "test agent" refers to any compound or molecule that is to be tested. As used herein, the terms, which are used interchangeably, refer to biological or chemical compounds such as simple or complex organic or inorganic molecules, peptides, proteins, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action.

"Treatment" or "treating" refers to therapy, inhibition of progression, or prophylaxis and particularly refers to administering medicine or performing medical procedures on a patient, for either prophylaxis (prevention) or to cure or reduce the extent of or likelihood of occurrence of the infirmity or malady or condition or event. In the present invention, the treatments using the agents described may be provided to slow or halt cartilage loss or damage, to slow or inhibit or reduce inflammation, or to inhibit or slow progression of osteoarthritis.

"Subject" or "patient" refers to a mammal, preferably a human, in need of treatment for a condition, disorder or disease.

In a specific embodiment, the term "about" means within 20%, preferably within 10%, and more preferably within 5% or even within 1%.

An "effective amount" or a "therapeutically effective amount" is an amount sufficient to decrease or prevent the symptoms associated with osteoarthritis or to stimulate or promote cartilage production or formation when compared to a baseline value. For example, an "effective amount" for therapeutic uses is the amount of the composition comprising an active compound herein required to provide reversal or inhibition of progression of osteoarthritis. Such effective amounts may be determined using routine optimization techniques and are dependent on the particular condition to be treated, the condition of the subject, the route of administration, the formulation, and the judgment of the practitioner and other factors evident to those skilled in the art. The dosage required for the liposomes, liposomal compositions and compounds of the invention is that which induces a statistically significant difference in cartilage degeneration or inflammation or symptoms of osteoarthritis between treatment and control groups. This difference may be seen, for example, as at least 1-2%, or any clinically significant slowing or halting of cartilage loss or damage, or inhibition or reduction of inflammation, or inhibition or slowing of progression of osteoarthritis or increased amount of cartilage present in the treatment group. General guidance for treatment regimens may be obtained from experiments carried out in vitro or in animal models of the disease. The "effective amount" or "therapeutically effective amount" may range from about 1 mg/Kg to about 200 mg/Kg in vivo, or more preferentially from about 10 mg/Kg to about 100 mg/Kg, and most preferentially from about 25 mg/Kg to about 50 mg/Kg in vivo.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Binding compounds can also be characterized by their effect on the activity of the target molecule. Thus, a "low activity" compound has an inhibitory concentration ($IC_{50}$) (for inhibitors or antagonists) or effective concentration ($EC_{50}$) (applicable to agonists) of greater than 1 μM under standard conditions. By "very low activity" is meant an $IC_{50}$ or $EC_{50}$ of above 100 μM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present.

Activity can be measured using methods known to those of ordinary skill in the art, e.g., by measuring any detectable product or signal produced by occurrence of an enzymatic reaction, or other activity by a protein being measured.

An individual "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of osteoarthritis. An individual having one or more of these risk factors has a higher probability of developing osteoarthritis than an individual without these risk factors.

"Prophylactic" or "therapeutic" treatment refers to administration to the subject of one or more of the subject compositions. If it is administered prior to clinical manifestation of the osteoarthritis then the treatment is prophylactic, i.e., it protects the subject against developing the osteoarthritis. The treatment is therapeutic if it is intended to diminish, ameliorate or maintain the existing osteoarthritis or side effects therefrom.

Liposomal Adenosine

Liposomal adenosine has not been previously administered for treatment of other medical problems or pathologies. A liposomal adenosine suspension was developed to prolong the half-life of adenosine in the joint and to enhance adenosine delivery. Liposomes have been used for drug delivery of a number of agents in the past and are currently licensed for treatment of infections (amphotericin) and cancer (daunorubicin) among other potential uses.

The purpose of suspending the adenosine in liposomes is two-fold. Adenosine is very short-lived in biological fluids due to rapid uptake and metabolism ($t_{1/2}$ in blood of adenosine=2-4 seconds). By administering adenosine in a liposomal preparation, the $t_{1/2}$ may be prolonged and thereby enhance the effect of the agent.

Adenosine $A_{2A}$ Receptors Mouse Model of Osteoarthritis

Mice lacking adenosine $A_{2A}$ receptors were recently demonstrated to have many symptoms consistent with osteoarthritis (difficulty walking and grabbing food and, for the males, difficulty mating with females). The joints of these mice were found to have developed osteoarthritis which increased in severity with age. Moreover, osteoarthritis developed in both male and female mice. Stimulation of adenosine receptors on chondrocytes (the cells that synthesize and maintain cartilage and which are primarily affected in osteoarthritis) suppresses the effects of inflammation on these cells. These findings demonstrate that adenosine $A_{2A}$ receptors are a useful target for the treatment of osteoarthritis.

A Closed Anterior Cruciate Ligament Injury Model of Osteoarthritis

A closed anterior cruciate ligament injury model of osteoarthritis in the rat was treated with liposomal suspensions of adenosine (or empty liposomes). The development of osteoarthritis was completely prevented in this model with the adenosine liposome preparation. The receptor specificity for these preparations may be established by co-administering with adenosine receptor specific antagonists and exploring the potential for development of more specific $A_{2A}$ adenosine receptor agonists in liposomal suspensions.

Discussion

The results presented herein provide evidence for a critical homeostatic mechanism in cartilage. Chondrocytes release ATP which is converted to adenosine extracellularly; the adenosine that is present prevents the phenotypic changes in chondrocytes associated with development of OA via engagement of A2AR. Disruption of this mechanism, as a result of inflammation, injury or aging with reduction of intracellular and extracellular ATP and extracellular adenosine, leads to phenotypic changes in chondrocytes with diminished expression of proteins involved in cartilage anabolism and greater expression of MMPs or collagens associated with cartilage hypertrophy. Moreover, these data demonstrate that replacement of adenosine by intra-articular injection of liposomal preparations of adenosine can restore the homeostatic equilibrium to cartilage following injury by engagement of A2AR.

Previous studies of equine cartilage explants demonstrate that removal of extracellular adenosine by treatment with adenosine deaminase significantly increased the release of NO, MMP-13, MMP-3 and GAG, a cartilage matrix breakdown product, and that an A2A agonist reversed this effect. These findings suggested that A2AR are tonically activated in articular chondrocytes preventing a shift in chondrocyte phenotype and chondrocyte-mediated damage to cartilage (Tesch et al., *Osteoarthritis and Cartilage/OARS, Osteoarthritis Research Society* 2004; 12:349-359). Although this finding was very interesting the marked difference between horse and other species with respect to purine metabolism (absent adenosine deaminase in the serum and nearly absent adenosine deaminase in various cell types in horses) suggested that horse tissues might be uniquely dependent upon extracellular adenosine to maintain homeostasis (Hovi et al., *Clinical and Experimental Immunology* 1976; 23:395-403; Tax et al., *Comp Biochem Physiol B* 1978; 61:439-441). Nonetheless, the results reported here indicate that both mouse and rat chondrocytes and cartilage, respectively, release ATP and adenosine which regulates chondrocyte phenotype in both inflammatory and non-inflammatory settings.

Although A2ARKO mice have been observed closely in numerous laboratories for many years their difficulty in mobility and the diminished use of their limbs in eating and mating was not remarked upon, nor the cause determined. The present data demonstrate that the difficulties in ambulation and other functions are most likely related to the premature development of OA in A2ARKO mice. When examined, the A2ARKO mice have radiologic and histologic characteristics of OA, including the loss of glycosaminoglycans, collagen, and cartilage matrix with fraying, or fibrillation, and destruction of cartilage matrix, increased metalloprotease gene expression and production, chondrocyte hypertrophy, and development of osteophytes. Interestingly, despite the loss of bone volume and substance in A2ARKO mice, previously ascribed to increased osteoclast activity in the bone of these mice, increased subchondral bone density and osteophyte formation were oberved, paradoxical findings often observed in patients with OA (Funck-Brentano et al., *Cytokine & Growth Factor Reviews* 2011; 22:91-97).

It has recently been appreciated that inflammation plays a central role in the development of OA and the findings reported here provide both confirmation of the hypothesis that inflammatory stimuli are central to the development of OA and evidence that tonic suppression of chondrocyte responses to inflammatory stimuli by A2AR ligation are important for joint homeostasis (Abramson et al., *Arthritis Research & Therapy* 2009; 11:227; Abramson et al., *J Rheumatol Suppl* 2004; 70:70-76). The demonstration that loss of A2AR leads to premature OA in mice suggests that targeting A2AR might provide a useful approach to the prevention of cartilage deterioration in patients with OA. Indeed, recent studies suggest that methotrexate treatment for patients with symptomatic knee OA provides at least symptomatic relief of OA and many of the anti-inflammatory effects of methotrexate are mediated by methotrexate-induced increases in extracellular adenosine levels acting at A2AR and A3R (Abou-Raya et al., *Annals of the Rheumatic Diseases* (2014); Wenham et al., *Rheumatology* 2013; 52:888-892; Chan et al., *Nature Reviews. Rheumatology* 2010; 6:175-178). In the therapeutic trials of MTX in OA no attempt was made to evaluate changes in cartilage homeostasis or changes in cartilage destruction and it is unlikely that the short time frame of these studies could have permitted any demonstration of the effects of methotrexate on progressive cartilage loss or other manifestations of OA.

Although a variety of effects of A2AR loss on chondrocytes and cartilage were observed, it is likely that the loss of A2AR in other cells present in the synovium contributed to the development of OA. For example, an increase in osteoclast differentiation and function leads to marked osteopenia in A2ARKO mice (Mediero et al., *Am J Pathol* 2012; 180:775-786). Similarly, adenosine acting at A2AR diminishes expression of a variety of inflammatory cytokines, such as IL-1 and TNFα, which likely play a role in the pathogenesis of OA (Hasko et al., *Frontiers in Immunology* 2013; 4:85). Thus, tonic A2AR-mediated suppression of inflammatory responses maintains joint homeostasis and one approach to preventing and treating OA is to target A2AR.

The studies reported herein used a liposomal formulation to prolong the presence of adenosine in the joint. Indeed, preliminary studies in which an aqueous solution of an A2AR agonist was injected into joints had no effect on joint swelling or development of structural changes in the joint after anterior cruciate ligament disruption (Corciulo, C and Cronstein B N, unpublished observation). The liposomal adenosine preparations were administered in both treatment and prevention groups of rats and prevented or treated joint swelling similarly. Surprisingly, there was less structural damage to the joints, as reflected by a better OARSI score, in the rats in which the initial injection of liposomal adenosine was delayed for a week after knee injury. The likely explanation for this effect is that the initial spike in inflammatory cytokines in the joint following injury of the knee which leads to chondrocyte expression of enzymes capable of destroying cartilage also leads to enhanced expression and function of A2AR in the injured tissue and, thus, a greater adenosine response. It has long been appreciated that ATP levels are decreased in OA chondrocytes and this reduction in cellular ATP content may result from the effects of age, injury or inflammation on mitochondria (Johnson et al., *Arthritis and Rheumatism* 2000; 43:1560-1570; Blanco et al., *Mitochondrion* 2004; 715-728; Loeser et al., *Current Opinion in Rheumatology* 2011; 23:492-496; Terkeltaub et al., *Mitochondrion* 2002; 1:301-319; Wang et al., *Arthritis & Rheumatology* 2015; 67:2141-2153). The results reported herein are consistent with these observations and suggest how reduced intracellular ATP in chondrocytes could lead to diminished ATP release into the extracellular space resulting in diminished resistance to the phenotypic changes in chondrocytes that are associated with development of OA. Nonetheless, the reduction in ATP release observed here is greater than the reduction in intracellular ATP levels suggesting the possibility that there is also a reduction in the capacity of chondrocytes to export ATP. There are a number of transporters that can export ATP to the extracellular space including ANKH and pannexins and ANKH expression is markedly reduced after exposure to IL-161 although the effect of injury or inflammatory mediators on pannexin-1 or pannexin-3 expression and function is less well established (Praetorius et al., *Purinergic Signalling* 2009; 5:433-446; Ho et al., *Science* 2000; 289:265-270). Interestingly, loss of pannexin-3 is protective in murine models of OA suggesting that this protein is not involved in the phenomena studied here (Moon et al., *J Mol Med (Berl)* 2015; 93:845-856). The observation that mice lacking expression of ANKH develop arthritis consistent with OA at an early age further supports the hypothesis that extracellular adenosine, derived from ATP, plays a homeostatic role in cartilage.

Further evidence for the importance of adenosine in maintenance of cartilage and joint homeostasis is provided by the spontaneous OA observed in NTSE KO mice. This ectoenzyme catalyzes the hydrolysis of AMP to adenosine and prior studies have demonstrated that the loss of CD73 activity leads to exaggerated inflammatory responses (Zeiser et al., *Am J Transplant* (2016) 64. Yegutkin et al., *Crit Rev Biochem Mol Biol* 2014; 49:473-497). Recently patients lacking CD73 have been described and while diffuse large artery calcification dominates the clinical picture nearly all of these patients suffer from a poorly characterized arthritis with associated periarticular calcification (St Hilaire et al., *The New England Journal of Medicine* 2011; 364:432-442; Ichikawa et al., *Journal of Clinical Rheumatology: practical reports on rheumatic & musculoskeletal diseases* 2015; 21:216-220). The rheumatic manifestations observed in these patients are consistent with the 16 notion that relative deficiencies in adenosine are deleterious for the structures of the joint.

Another ectoenzyme, ENTPD1, which catalyzes the hydrolysis of ATP and ADP to AMP, also plays an important role in endogenous suppression of inflammation although there are a number of other extracellular phosphatases capable of hydrolyzing ATP, such as tissue non-specific alkaline phosphatase (TNAP) (Yegutkin et al., *Crit Rev Biochem Mol Biol* 2014; 49:473-497). Although ENTPD1 KO mice did not develop OA it is likely that these other phosphatases hydrolyzed sufficient ATP to adenosine to maintain homeostasis. Adenosine, acting at A2AR, is an important homeostatic regulator of chondrocytes and cartilage and adenosine repletion represents a novel approach to treating OA.

Adenosine and its Receptors

Adenosine, a potent endogenous physiological mediator, regulates a wide variety of physiological processes via interaction with one or more of four G protein-coupled receptors ($A_1$, $A_{2A}$, $A_{2B}$, and $A_3$), expressed on many cell types, including neutrophils, macrophages, fibroblasts, and endothelial cells. Because adenosine $A_{2A}$ receptors inhibit the formation of giant cells from peripheral blood monocytes in vitro it was determined that adenosine, acting through one or another of these receptors, regulated the formation of osteoclasts.

In one embodiment, agents that interact with (e.g., bind to) and block, agonize or stimulate an adenosine receptor, in particular, $A_{2A}$ (e.g., a functionally active fragment), are identified in a cell-based assay system. In accordance with this embodiment, cells expressing an adenosine receptor, a fragment of an adenosine receptor, an adenosine receptor related polypeptide, or a binding fragment thereof, are contacted with a candidate compound or a control compound and the ability of the candidate compound to interact with the receptor or fragment thereof is determined. Alternatively, the ability of a candidate compound to compete for binding with a known ligand or compound known to bind the receptor is measured. If desired, this assay may be used to screen a plurality (e.g. a library) of candidate compounds. The cell, for example, can be of prokaryotic origin (e.g., *E. coli*) or eukaryotic origin (e.g., yeast, insect or mammalian). Further, the cells can express the receptor endogenously or be genetically engineered to express the receptor, a binding fragment or a receptor fusion protein. In some embodiments, the receptor or fragment thereof, or the candidate compound is labeled, for example with a radioactive label (such as $^{32}$P, $^{35}$S or $^{125}$I) or a fluorescent label (such as fluorescein isothiocyanate, rhodamine, phycoerythrin, phycocyanin, allophycocyanin, o-phthaldehyde or fluorescamine) to enable detecting an interaction between the $A_{2A}$ receptor and a candidate compound. The ability of the candidate compound to interact directly or indirectly with a receptor or binding fragment thereof or a fusion protein or to modulate the activity of the receptor can be determined by methods known to those of skill in the art. For example, the interaction or modulation by a candidate compound can be determined by flow cytometry, a scintillation assay, immunoprecipitation or western blot analysis, based on the present description, or by a competitive radioreceptor assay.

Selecting the compounds that interact with or bind to an adenosine receptor or otherwise agonize or stimulate the receptor may be performed in multiple ways. The compounds may first be chosen based on their structural and functional characteristics, using one of a number of approaches known in the art. For instance, homology modeling can be used to screen small molecule libraries in order to determine which molecules are candidates to interact with the receptor thereby selecting plausible targets. The compounds to be screened can include both natural and synthetic ligands. Furthermore, any desired compound may be examined for its ability to interact with or bind to the receptor.

Binding to or interaction with adenosine receptors may be determined by performing an assay such as, for example, a binding assay between a desired compound and an adenosine receptor. In one aspect, this is done by contacting said compound to an adenosine receptor and determining its dissociation rate. Numerous possibilities for performing binding assays are well known in the art. The indication of a compound's ability to bind to an adenosine receptor is determined, e.g., by a dissociation rate, and the correlation of binding activity and dissociation rates is well established in the art. For example, the assay may be performed by radio-labeling a reference compound, or other suitable radioactive marker, and incubating it with the cell bearing an adenosine receptor, in particular, an $A_1$ or $A_{2A}$. Test compounds are then added to these reactions in increasing concentrations. After optimal incubation, the reference compound and receptor complexes are separated, e.g., with chromatography columns, and evaluated for bound $^{125}$I-labeled peptide with a gamma ($\gamma$) counter. The amount of the test compound necessary to inhibit 50% of the reference compound's binding is determined. These values are then normalized to the concentration of unlabeled reference compound's binding (relative inhibitory concentration $(RIC)^{-1}$=concentration$_{test}$/concentration$_{reference}$). A small $RIC^{-1}$ value indicates strong relative binding, whereas a large $RIC^{-1}$ value indicates weak relative binding. See, for example, Latek et al., *Proc. Natl. Acad. Sci. USA*, Vol. 97, No. 21, pp. 11460-11465, 2000. An adenosine receptor agonist mimic may be computationally evaluated and designed by means of a series of steps in which chemical groups or fragments are screened and selected for their ability to associate with the individual binding pockets or interface surfaces of the protein (e.g. the $A_{2A}$ receptor). One skilled in the art may employ one of several methods to screen chemical groups or fragments for their ability to associate with the adenosine receptor.

This process may begin by visual inspection of, for example, the protein/protein interfaces or the binding site on a computer screen based on the available crystal complex coordinates of the receptor, including a protein known to interact with selected fragments or chemical groups may then be positioned in a variety of orientations, or docked, at an individual surface of the receptor that participates in a protein/protein interface or in the binding pocket. Docking may be accomplished using software such as QUANTA and SYBYL, followed by energy minimization and molecular dynamics with standard molecular mechanics forcefields, such as CHARMM and AMBER (AMBER, version 4.0 (Kollman, University of California at San Francisco, copyright, 1994); QUANTA/CHARMM (Molecular Simulations, Inc., Burlington, Mass., copyright, 1994)). Specialized computer programs may also assist in the process of selecting fragments or chemical groups. These include: GRID (Goodford, 1985, *J. Med. Chem.* 28:849-857), available from Oxford University, Oxford, UK; MCSS (Miranker & Karplus, 1991, Proteins: Structure, Function and Genetics 11:29-34), available from Molecular Simulations, Burlington, Mass.; AUTODOCK (Goodsell & Olsen, 1990, Proteins: Structure, Function, and *Genetics* 8:195-202), available from Scripps Research Institute, La Jolla, Calif.; and DOCK (Kuntz et al., 1982, *J. Mol. Biol.* 161:269-288), available from University of California, San Francisco, Calif. Once suitable chemical groups or fragments that bind to an adenosine receptor have been selected, they can be assembled into a single compound or agonist. Assembly may proceed by visual inspection of the relationship of the fragments to each other in the three-dimensional image displayed on a computer screen in relation to the structure coordinates thereof. This would be followed by manual model building using software such as QUANTA or SYBYL. Useful programs to aid one of skill in the art in connecting the individual chemical groups or fragments include: CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182-196), available from the University of California, Berkeley, Calif.; 3D Database systems such as MACCS-3D (MDL Information Systems, San Leandro, Calif.). This area is reviewed in Martin, 1992, *J. Med. Chem.* 35:2145-2154); and HOOK (available from Molecular Simulations, Burlington, Mass.). Instead of proceeding to build an adenosine receptor agonist mimic, in a step-wise fashion one fragment or chemical group at a time, as described above, such compounds may be designed as a whole or 'de novo' using either an empty binding site or the surface of a protein that participates in protein/protein interactions or optionally including some portion(s) of a known activator(s). These methods include: LUDI (Bohm, 1992, *J. Comp. Aid. Molec. Design* 6:61-78), available from Molecular Simulations, Inc., San Diego, Calif.; LEGEND (Nishibata et al., 1991, *Tetrahedron* 47:8985), available from Molecular Simulations, Burlington, Mass.; and Leap-Frog (available from Tripos, Inc., St. Louis, Mo.). Other molecular modeling techniques may also be employed in accordance with this invention. See, e.g., Cohen et al., 1990, *J. Med. Chem.* 33:883-894. See also, Navia & Murcko, 1992, *Current Opinions in Structural Biology* 2:202-210.

Once a compound has been designed by the above methods, the efficiency with which that compound may bind to or interact with the adenosine receptor protein may be tested and optimized by computational evaluation. Agonists may interact with the receptor in more than one conformation that is similar in overall binding energy. In those cases, the deformation energy of binding is taken to be the difference between the energy of the free compound and the average energy of the conformations observed when the inhibitor binds to the receptor protein.

A compound selected for binding to the adenosine receptor may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the compound and the receptor protein when the mimic is bound to it preferably make a neutral or favorable contribution to the enthalpy of binding. Specific computer software is available in the art to evaluate compound deformation energy and electrostatic interaction. Examples of programs designed for such uses include: Gaussian 92, revision C (Frisch, Gaussian, Inc., Pittsburgh, Pa. copyright 1992); AMBER, version 4.0 (Kollman, University of California at San Francisco, copyright 1994); QUANTA/CHARMM (Molecular Simulations, Inc., Burlington, Mass., copyright 1994); and Insight II/Discover (Biosym Technologies Inc., San Diego, Calif., copyright 1994). These programs may be implemented, for instance, using a computer workstation, as are well-known in the art. Other hardware systems and software packages will be known to those skilled in the art.

Once an adenosine receptor modulating compound, such as an agonist, has been optimally designed, for example as described above, substitutions may then be made in some of its atoms or chemical groups in order to improve or modify its binding properties, or its pharmaceutical properties such as stability or toxicity. Generally, initial substitutions are conservative, i.e., the replacement group will have approximately the same size, shape, hydrophobicity and charge as the original group. Substitutions known in the art to alter conformation should be avoided. Such altered chemical compounds may then be analyzed for efficiency of binding to the receptor by the same computer methods described in detail above.

Candidate Compounds and Agents

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, *Anticancer Drug Des.* 12:145; U.S. Pat. Nos. 5,738,996 and 5,807,683).

Phage display libraries may be used to screen potential ligands or adenosine receptor modulators such as agonists. Their usefulness lies in the ability to screen, for example, a library displaying a large number of different compounds. For use of phage display libraries in a screening process, see, for instance, Kay et al., *Methods*, 240-246, 2001. An exemplary scheme for using phage display libraries to identify compounds that bind to or interact with an adenosine receptor may be described as follows: initially, an aliquot of the library is introduced into microtiter plate wells that have previously been coated with the target protein, e.g. $A_1$ or $A_{2A}$ receptor. After incubation (e.g., 2 hours), the nonbinding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for the adenosine $A_{2A}$ receptor may be obtained by performing ELISAs. One skilled in the art can easily perform these experiments. In one aspect, an $A_1$ or $A_{2A}$ receptor molecule used for any of the assays may be a recombinant $A_1$ or $A_{2A}$ receptor protein, or an $A_1$ or $A_{2A}$ fusion protein, an analog, derivative, or mimic thereof.

Examples of methods for the synthesis of molecular libraries can be found in the art, for example in DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carrell et al., 1994, *Angew. Chem. Int. Ed. Engl.* 33:2059; Carell et al., 1994, *Angew. Chem. Int. Ed. Engl.* 33:2061; and Gallop et al., 1994, *J Med. Chem.* 37:1233.

Libraries of compounds may be presented, e.g., in solution (Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223,409), plasmids (Cull et al., 1992, *Proc. Natl. Acad. Sci. USA* 89:1865-1869) or phage (Scott and Smith, 1990, *Science* 249:386-390; Devlin, 1990, *Science* 249:404-406; Cwirla et al., 1990, *Proc. Natl. Acad. Sci. USA* 87:6378-6382; and Felici, 1991, *J Mol. Biol.* 222:301-310).

The methods of screening compounds may also include the specific identification or characterization of such compounds, whose effect on osteoarthritis is determined by the methods described above. If the identity of the compound is known from the start of the experiment, no additional assays are needed to determine its identity. However, if the screening for compounds that modulate the adenosine $A_{2A}$ receptor is done with a library of compounds, it may be necessary to perform additional tests to positively identify a compound that satisfies all required conditions of the screening process. There are multiple ways to determine the identity of the compound. One process involves mass spectrometry, for which various methods are available and known to the skilled artisan (e.g. the neogenesis website). Neogenesis' ALIS (automated ligand identification system) spectral search engine and data analysis software allow for a highly specific identification of a ligand structure based on the exact mass of the ligand. One skilled in the art can also readily perform mass spectrometry experiments to determine the identity of the compound.

Therapeutic and Prophylactic Compositions and Their Use

Candidates for therapy with the agents identified by the methods described herein are patients suffering from osteoarthritis.

The invention provides methods of treatment featuring administering to a subject an effective amount of an agent or compound of the invention. The compound is preferably substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. Accordingly, the agents identified by the methods described herein may be formulated as pharmaceutical compositions to be used for prophylaxis or therapeutic use to treat these patients.

Various delivery systems are known and can be used to administer a compound of the invention, e.g., encapsulation in liposomes, microparticles, or microcapsules. The compound can be delivered in a vesicle, in particular a liposome (Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327) Many suitable liposome formulations are known to those skilled in the art, and may be used, such as those described in U.S. Pat. No. 5,190,762.

The compositions of the present invention may also be administered locally to sites in subjects, both human and other vertebrates, such as a joint, particularly directly into the synovial fluid of a joint. The administration of the compositions of the present invention may be pharmacokinetically and pharmacodynamically controlled by calibrating various parameters of administration, including the frequency, dosage, duration, mode and route of administration. Variations in the dosage, duration and mode of administration may also be manipulated to produce the activity required.

The compositions are administered in a manner compatible with the agent or compound selected for treating the subject, the dosage formulation, and in a therapeutically effective amount. If one desires to achieve the desired effect in vitro, the effective amounts may range from about 0.1 nM to about 10 µM, more preferably about 0.1 nM to about 5 µM, and most preferably from about 0.1 nM to about 1 nM. The desired effect refers to the effect of the agent or compound on reducing or inhibiting cartilage damage, inflammation and osteoarthritis. Moreover, the quantity of the adenosine or adenosine receptor agonist to be administered depends on the subject to be treated or the extent or severity of osteoarthritis. Precise amounts of active ingredient required to be administered depend on the judgment of the practitioner and are peculiar to each individual. However, suitable dosages to achieve the desired therapeutic effect in vivo may range from about 0.1 mg/kg body weight per day to about 200 mg/kg body weight per day, or from about 1.0 mg/kg body weight per day to about 100 mg/kg body weight per day, preferably about 5 mg/kg or 10 mg/kg or 25 mg/kg body weight per day to about 50 mg/kg body weight per day. In a particular embodiment, the term "about" means within 20%, preferably within 10%, and more preferably within 5%. The preferred dose will depend on the particulars of administration. However, dosage levels are highly dependent on the nature of the disease or situation, the condition of the subject, the judgment of the practitioner, and the frequency and mode of administration. Suitable regimes for initial administration and further administration are also variable, but are typified by an initial administration followed by repeated doses at one or more hour intervals by a subsequent injection or other administration.

It will be understood that the appropriate dosage of the substance should suitably be assessed by performing animal model tests, where the effective dose level (e.g., $ED_{50}$) and the toxic dose level (e.g. $TD_{50}$) as well as the lethal dose level (e.g. $LD_{50}$ or $LD_{10}$) are established in suitable and acceptable animal models. Further, if a substance has proven efficient in such animal tests, controlled clinical trials should be performed.

The invention also provides a pharmaceutical pack or kit comprising one or more containers filled with one or more of the ingredients of the liposomes or liposomal compositions. Optionally associated with such containers can be a notice in the form prescribed by a governmental agency regulating the manufacture, use or sale of pharmaceuticals or biological products, which notice reflects (a) approval by the agency of manufacture, use or sale for human administration, (b) directions for use, or both.

Effective Doses

Toxicity and therapeutic efficacy of agents or compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds or agents that exhibit large therapeutic indices are preferred. While compounds that exhibit toxic side effects can be used, care should be taken to design a delivery system that targets such agents or compounds to the site of affected tissue, e.g. a joint, in order to minimize potential damage to unaffected cells and, thereby, reduce side effects.

The data obtained from cell culture assays and animal studies can be used in formulating a dose range for use in humans. For any compound used in the method of the invention, the therapeutically effective dose can be estimated initially from cell culture assays. A dose can be formulated in animal models. Such information can be used to optimize efficacious doses for administration to humans.

In addition, in vitro assays may optionally be employed to help identify optimal dosage ranges. The precise dose to be employed in the formulation will also depend on the seriousness of the disease or disorder, e.g. the osteoarthritis, and should be decided according to the judgment of the practitioner and each subject's circumstances. Normal dose ranges used for particular therapeutic agents employed for specific diseases can be found in the Physicians' Desk Reference 54th Edition (2000).

EXAMPLES

The following examples are set forth to provide those of ordinary skill in the art with a description of how to make and use the methods and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of Liposomes

Liposomes were prepared using soybean oil at a 5.5:1 weight ratio with lipid phase consisting of phosphatidyl choline and cholesterol (1:0.5 by molar ratio) the day before the injection. Ethanol (100 mg) was added to soybean oil (0.5 gr) and adenosine (300 mg). The lipid phase (90 mg)

containing phosphatidyl choline and cholesterol (1:0.5 by molar ratio) was added to the previous solution and emulsified at 15,000 rpm for 10 minutes. Saline (10 ml) along with glycerin (250 mg) was added to the lipid phase and was homogenized at 15,000 rpm for 20 minutes. It was followed by sonication for 1 minute at 100% duty cycle. Liposomes containing ZM241385, CGS21680, Dipyridamole are prepared in a similar fashion. The dose injected in each rat knee was 1 mg/Kg. The adenosine retention in liposome particles was tested by using HPLC as previously described by Cronstein et al., *Journal of Experimental Medicine*, 1983; 158:1160-1177.

Example 2

Induction of Post-traumatic Osteoarthritis (PTOA) in Rats and Treatment with Adenosine in a Liposome Formulation
Materials and Methods The PTOA model is a non-invasive method for inducing anterior cruciate ligament (ACL) rupture in rat knees in vivo with a single load of tibia compression overload. For tibial loading, animals were anesthetized and maintained on 1-3% isoflurane. The left hindlimb was positioned between two loading platens: an upper platen that held the flexed ankle at approximately 30 degrees of dorsiflexion and a lower platen that held the flexed knee. The platens were aligned vertically in an electromagnetic materials testing machine (Bose ElectroForce 3200, Eden Prairie, Minn.). A preload of 1 N was applied to the knee before a single dynamic axial compressive load was applied.

Rats were treated with a liposome formulation containing high concentration of adenosine (10 mg/Kg), or with empty liposome, or with saline for 8 weeks (6 animals for each group). The animals were separated in two main cohorts, the prevention group receiving the injection right after the ACL rupture, and the treatment group receiving the first injection after 7 days. The following injections were performed every 10 days. Prior to intraarticular (IA) injection, the site was prepared aseptically for injection. The site was defined by palpating patella externally, and then injecting 100 μl of solution through the patellar ligament into the joint space.

Figure 1B:
Figure 1C:
Figure 2A:
FIG. 2(A,B,C) provides representative microCTs of femoral condyles from a control knee and a knee treated with either liposomes containing saline or liposomes containing adenosine. The smooth surface of the cartilage in the control knee (FIG. 2A) and the osteoarthritis knee treated with adenosine-containing liposomes (FIG. 2C) is apparent. Similarly, representative microCT images of uninvolved (control) and saline-containing or adenosine-containing liposomes demonstrate the same. Destructive changes are apparent in the bone of the osteoarthritis knee treated with saline-containing liposomes (FIG. 2B) in contrast to the condyles treated with the adenosine containing liposomes.
Figure 2B:
Figure 2C:

After injury, rats were given a subcutaneous injection of buprenorphine (0.1 mg/kg body weight) for analgesia. After loading animals were returned to normal cage activity. At the end point the blood was collected by a cardiac puncture and both legs are harvested for immunohistochemistry and micro-computed tomography analysis in order to evaluate the alterations in bone and cartilage features.
Results FIG. 1(A,B,C) provides representative photographs of femoral condyles from a control knee and a knee treated with either liposomes containing saline or liposomes containing adenosine. The smooth surface of the cartilage in the control knee and the osteoarthritis knee treated with adenosine-containing liposomes is apparent. Similarly, representative microCT images of uninvolved (control) and saline-containing or adenosine-containing liposomes. Destructive changes are apparent in the bone of the osteoarthritis knee treated with saline-containing liposomes in contrast to the condyles treated with the adenosine containing liposomes. FIG. 2(A,B,C) provides representative microCTs of femoral condyles from a control knee and a knee treated with either liposomes containing saline or liposomes containing adenosine. The smooth surface of the cartilage in the control knee and the osteoarthritis knee treated with adenosine-containing liposomes is apparent. Similarly, representative microCT images of uninvolved (control) and saline-containing or adenosine-containing liposomes. Destructive changes are apparent in the bone of the osteoarthritis knee treated with saline-containing liposomes in contrast to the condyles treated with the adenosine containing liposomes.

Example 3

Induction of Post-traumatic Osteoarthritis (PTOA) in Rats and Treatment with an Adenosine Receptor Agonist in a Liposome Formulation.
Materials and Methods The PTOA model is a non-invasive method for inducing anterior cruciate ligament (ACL) rupture in rat knees in vivo with a single load of tibia compression overload. For tibial loading, animals were anesthetized and maintained on 1-3% isoflurane. The left hindlimb was positioned between two loading platens: an upper platen that held the flexed ankle at approximately 30 degrees of dorsiflexion and a lower platen that held the flexed knee. The platens were aligned vertically in an electromagnetic materials testing machine (Bose ElectroForce 3200, Eden Prairie, Minn.). A preload of 1 N was applied to the knee before a single dynamic axial compressive load was applied.

Rats were treated with a liposome formulation containing a high concentration of an adenosine $A_{2A}$ receptor agonist, CGS21680 (c. 10 mg/Kg), or with an empty liposome, or with saline for 8 weeks (6 animals for each group). The animals were separated into two main cohorts, the prevention group receiving the injection right after the ACL rupture, and the treatment group receiving the first injection after 7 days. The following injections were performed every 10 days. Prior to intraarticular (IA) injection, the site was prepared aseptically for injection. The site was defined by palpating the patella externally, and then injecting 100 μl of solution through the patellar ligament into the joint space.

After injury, rats were given a subcutaneous injection of buprenorphine (0.1 mg/kg body weight) for analgesia. After loading animals were returned to normal cage activity. At the end point the blood was collected by a cardiac puncture and both legs are harvested for immunohistochemistry and micro-computed tomography analysis in order to evaluate the alterations in bone and cartilage features.
Results FIG. 3(A,B,C,D) provides representative microCT images of the femur and tibia from a control knee and an arthritic knee treated with either saline, empty liposomes or liposomes containing an adenosine $A_{2A}$ receptor agonist, in this case CGS21680. The smooth surface of the cartilage in the control knee and the osteoarthritis knee treated with liposomes containing an adenosine $A_{2A}$ receptor agonist, in this case CGS21680 is apparent. Destructive changes are apparent in the bones of the osteoarthritis knees treated with saline or empty liposomes in contrast to the bones treated with liposomes containing the adenosine $A_{2A}$ receptor agonist, in this case CGS21680.

Example 4

Background

Aggrecan, also known as cartilage-specific proteoglycan core protein (CSPCP) or chondroitin sulfate proteoglycan 1, is a protein that is an integral part of the extracellular matrix in cartilagenous tissue, and it withstands compression in cartilage. It is a critical component for cartilage structure and the function of joints. It also plays an important role in mediating chondrocyte-chondrocyte and chondrocyte-matrix interactions through its ability to bind hyaluronan. It provides intervertebral disc and cartilage with the ability to resist compressive loads. The synthesis and degradation of aggrecan are related to cartilage deterioration during joint injury, disease, and aging. Degradation has been associated with the development of arthritis. Articular cartilage contains up to 10% proteoglycan by weight, most of which is aggrecan, and its loss is an early sign of the disease.

Methods and Results

Following sacrifice, rat knees were assessed by gross inspection, microCT (with and without staining of rat knees by immersion in a 40% solution of Hexabrix for 5 minutes at room temperature). Contrast and gain of microCT images allows for visualization of Hexabrix-stained cartilage, and following use of the Amira software, volume was calculated. Both surface area and volume of articular cartilage was quantitated from reconstructed three-dimensional images of the cartilage using CT-Vox software (Bruker Corporation) and Amira software (USA). (Xie et al., *Osteoarthritis and Cartilage/OARS, Osteoarthritis Research Society* 2009; 17:313-320). FIG. 4C provides the volume of cartilage in knees treated with liposomes containing CGS21680 expressed as the % of cartilage in the unaffected, untreated knee in that same rat. As noted, the tibial cartilage of all three rats was increased as compared to the normal, unaffected knee, and the femoral cartilage was increased in two of the three rats treated with liposomal CGS21680.

Figure 4A:
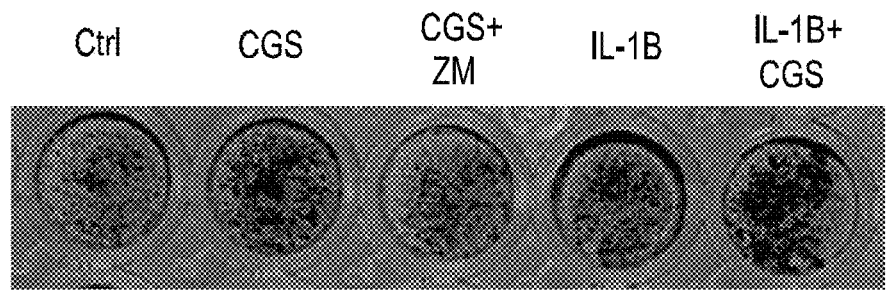
FIG. 4A provides representative tissue culture wells stained for aggrecan with alcian blue (dark areas). As can be seen the greatest amount of alcian blue-stained material is in the wells in which chondrocytes were treated with CGS21680 (1 µM) in the absence or presence of IL-1 (a treatment which diminishes aggrecan production). Following digital quantitation of alcian-blue stained aggrecan in the tissue wells aggrecan levels are expressed as % control (+SEM) (4B).
Figure 4B:
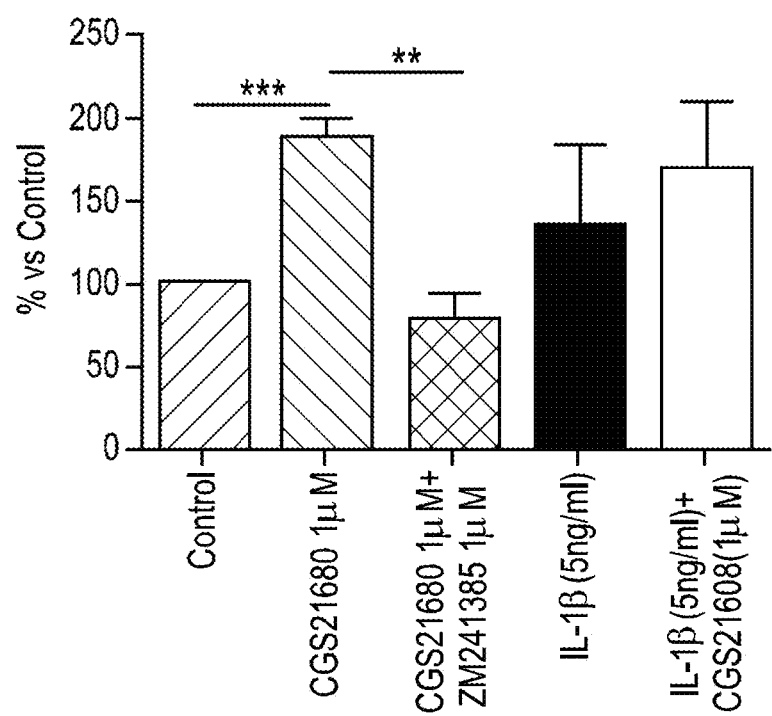
FIG. 4(A,B,C) demonstrates that a liposomal composition containing an adenosine $A_{2A}$ receptor agonist promotes cartilage formation.
FIG. 4C provides the volume of cartilage in the knees treated with liposomes containing CGS21680 expressed as the % of cartilage present in the unaffected, untreated knee in the same subject. The amount of tibial cartilage in all three rats was increased as compared to the normal, unaffected knee, and the amount of femoral cartilage was increased in two of the three rats treated with liposomal CGS21680 as compared to the normal, unaffected knee.

In preliminary experiments, stimulation of neonatal murine chondrocytes with an $A_{2A}$ receptor agonist (CGS21680, 1 μM) provided a nearly two-fold increase in aggrecan expression, as determined by Alcian Blue staining of the cultured chondrocyte matrix. (Gosset et al., *Nat Protoc* 2008; 3:1253-1260). FIG. 4A shows the representative tissue culture wells stained for aggrecan with alcian blue (dark areas). As can be seen, the greatest amount of alcian blue-stained material is in the wells in which chondrocytes were treated with CGS21680 (1 μM) in the absence or presence of IL-1 (a treatment which diminishes aggrecan production). Following digital quantitation of alcian-blue stained aggrecan in the tissue wells, aggrecan levels are expressed as % control (±SEM) as provided in FIG. 4B.

Example 5

Materials and Methods

Materials

ZM241385 (an A2AR antagonist), PSB1115 (an A2BR antagonist) and VUF5574 (an A3R antagonist) were obtained from TOCRIS (MI, USA). Mouse and rat recombinant Il-1β was obtained from R&D Systems (MN, USA). Antibodies: Rb-MMP-13 was purchased from ABCAM (MA, USA), Rb-NTSE/CD73 from Cell signaling (MA, USA) and Rb-Collagen-X from Millipore (MA, USA) and secondary antibody HRP conjugate were obtained from SantaCruz (CA, USA). Hexabrix was purchased from Guerbet (IN, USA). Paraformaldehyde (PFA) 32% was obtained from Electron Microscopy Sciences (PA, USA). RIPA buffer, Ethylenediaminetetraacetic acid (EDTA), bovine serum albumin, SIGMAFAST™ 3,3'-Diaminobenzidine tablets, Anti-Rabbit IgG-FITC antibody, Anti-Rabbit IgG-TRITC antibody, Amphotericin B, cholesterol, phosphatydil choline from egg yolk, ethanol, glycerol, adenosine and ascorbic acid, murine primer sequences (Tab. 1) were purchased from Sigma Aldrich (MO, USA). Alexa Fluor 555 phalloidin, DMEM-F12, DMEM, penicillin-streptomycin and fetal bovine serum were purchased from Life technology (NY, USA). ATP determination kit was purchased from Thermo Fisher (MA, USA). The kit for RNA extraction was purchased from QIAGEN (CA, USA). The reverse transcription kit was purchased from Applied Biosystem (CA, USA). The Brilliant FAST SYBR Green were obtained from Agilent Technologies (CA, USA).

Animals

Mice and rats employed in this study were kept under regular lighting conditions (12 h light/dark cycles) and given food and water ad libitum. Adenosine A2A receptor knock-out (A2ARKO) mice and CD73 knockout (CD73KO) mice were kindly provided respectively by Dr. Jiang Fan Chen (Boston University School of Medicine, Boston, Mass.) and Dr. Linda Thompson (Oklahoma Medical Research Foundation, Oklahoma City, Okla.). Male and female A2ARKO and CD73KO mice were bred onto a C57BL/6 background (≥10 backcrosses) in the New York University School of Medicine Animal Facility. Wild type (WT) mice were all maintained on the C57BL/6 background by the breeder (Taconic Laboratories, Albany, N.Y.). Genotyping was performed by PCR, as previously reported (Montesinos et al., *The American Journal of Pathology* 2002; 160:2009-2018). WT and A2ARKO newborn mice were used for chondrocyte extraction from knee joint. Mice were sacrificed by CO2 narcosis. Sprague Dawly male rats were used in the experimental OA induction (n=5-6 for each group) and for tibia collection in the ex vivo tibia loading experiment (n=10). All protocols for experimental procedures involving the use of animals were approved by the New York University School of Medicine Institutional Animal Care and Use Committee.

Motor Test

In order to test for and quantitate any motor impairment, two different motor tests were performed on WT and A2ARKO 25 weeks old mice. Mice (n=5 for each group) were acclimated in the apparatus for 1 hour before the test.

Open Field Test

Spontaneous locomotor activity was analyzed using the open-field test. Mice were placed into the center of a chamber 25×25×25 cm to allow free exploration. The experiments were performed for 30 minutes on 2 consecutive days. Total travel distance, velocity, time spent in the border and immobility time were measured by computerized analysis at 10 minute intervals. The number of rearings was quantitated in the first 10 minute interval.

Mice behavior was recorded and videos were analyzed by use of EthoVision XT software (Noldus, The Netherlands).

Rotarod Test

Mice were placed on a rotarod apparatus (AccuRotor Rota Rod-Accuscan Instruments, Columbus, Ohio) and tested for 5 minutes with a constant acceleration from 4 to 40 rpm. The latency to fall was registered for each animal. To exclude differences in learning skills between the two groups of mice, each group was assessed over three trials per day for 2 consecutive days. Mice were given a 30 minute inter-trial rest interval.

Tibial Explant Loading Experiments 14 to 19 week old male Sprague-Dawly rats were sacrificed and their tibias were harvested. The soft tissue was removed from the bone and the proximal tibia was cut in the growth plate region by using a Low Speed Diamond Wheel Saw-Model 650 (South Bay Technologies, CA, USA). Tibia surface was cut separating the medial and the lateral condyle. Samples were incubated in media containing DMEM-F12, FBS 10%, 100 ug/ml of ascorbic acid, 2 mM of L-glutamate, 1% of Penicillin, Streptomycin and amphotericin. The explants were incubated with or without IL-1β (5 ng/ml) for 24 hours. After incubation the samples were placed in a glass plate in new media without FBS. The loading was programmed using the block waveform feature in Wintest 7 software of BOSE Electroforce 3200 system (Bose Inc., MN, USA). The specimens were preloaded with uniaxial compressive load that was applied at 0.005 mm/s loading rate under displacement control up to 0.01 mm. Samples undergo cyclic load at 2 Hz for 1800 cycles at 1.5N compressive load under load control. Dwell for 2700s immediately after the end of 1800th cycle. Media samples were collected after 1, 10 and 15 minutes during loading and 15 and 30 minutes after loading. Samples collected for ATP assay were stored immediately on ice. Samples used for adenosine 20 extraction were collected in tubes containing Trichloroacetic acid (1:1, v/v).

Induction of Post-traumatic OA (PTOA) in Rats and Treatment With a Liposomal Adenosine 22 Formulation The PTOA model used is a non-invasive method for inducing anterior cruciate ligament (ACL) rupture in rat knees in vivo with a single load of tibial compression. The procedure was performed under anesthesia (1-3% isoflurane) as previously described (Ramme et al., Osteoarthritis and Cartilage/OARS, Osteoarthritis Research Society (2016)). Rats were treated with intra-articular injections of 100 µl of a liposomal suspension containing a high concentration of adenosine (10 mg/Kg), empty liposomes or with saline for 8 weeks. In some experiments rats were injected intraarticularly with 100 µl of liposomal suspensions of adenosine plus ZM241385 (1 mg/Kg), adenosine plus PSB1115 (1 mg/Kg), adenosine plus VUF5574 (1 mg/kg). The animals were separated into two main cohorts, the prevention group received injections commencing immediately after ACL rupture, and the treatment group received the first injection 7 days after ACL rupture. Injections were performed every 10 days thereafter in both groups. Knee swelling and weight in the rats were measured before every injection. At the end of the experiment rats were sacrificed and both legs were harvested for immunohistochemistry and micro-computed tomography (µCT) analysis.

Liposome Preparation

Liposomes were prepared fresh the day before injection. Ethanol was added to soybean oil containing adenosine, or adenosine plus adenosine receptor antagonists. The lipid phase containing phosphatidyl choline and cholesterol (1:0.5 by molar ratio) was added to the previous solution and emulsified at 15000 rpm for 10 minutes. Saline along with glycerin was then added to the lipid phase and was homogenized at 15000 rpm for 20 minutes followed by sonication for 1 minute at 100% duty cycle.

Measurement of Adenosine Concentration by HPLC Analysis

Extraction and quantification of supernatant adenosine by reverse phase HPLC from media samples were conducted as previously described (Cronstein et al., The Journal of Clinical Investigation 1993; 92:2675-2682).

To test adenosine retention in liposomes, liposome particles were centrifuged at 100,000 g in an ultracentrifuge (Optima L-90K Beckman Coulter) for 15 min at 4° C., free adenosine was collected from the supernate and different dilutions were tested by HPLC. 73% of the adenosine was retained in the liposomes.

Histology and Immunohistochemistry

Mouse Sample Preparation

After sacrifice, both hind legs were excised from WT and A2ARKO mice (4 animals for each group). Left hind limbs, assigned to immunohistochemistry analysis, were cleaned of soft tissue, placed into 4% PFA for 48 hours, and decalcified in 10% EDTA for 4 weeks. Paraffin-embedded histological sections (5 µm) were cut, mounted and prepared for analysis with H&E and Safranin 0/Fast green staining to assay different cartilage components. Collagen X, MMP-13 were detected in cartilage by immunohistochemistry. Briefly, joint sections were deparaffinized by xylene and re-hydrated in decreasing ethanol concentrations. Sections were depleted of endogenous peroxidase activity with 3% H2O2 in methanol, then blocked with PBST containing bovine serum albumin (1%) and FBS (5%) for 60 min. Sections were incubated overnight with rabbit antibody (1:200 dilution) specific for each protein under study. After rinsing with phosphate buffered saline (PBS), horseradish peroxidase (HRP)-conjugated secondary antibody was applied and stained with diaminobenzidine (DAB) kit. Slides were scanned using a Leica microscope equipped with Slidepath Digital Image Hub version 3.0 Software. Assessment of OA was performed by evaluation of Safranin-0 stained slides in a blinded fashion. OARSI score was determined blindly as previously described taking into account the severity of cartilage degradation, cartilage calcification, presence of osteophytes and their size (Gerwin et al., Osteoarthritis and Cartilage/OARS, Osteoarthritis Research Society 2010; 18(Suppl 3):524-34).

Rat Samples

After sacrifice both legs were excised and fixed with 4% PFA for 48 hours and then preserved in 70% ethanol. After µCT analysis the samples were washed with PBS and decalcified in 10% EDTA for 4 weeks. Histology and immunohistochemistry were performed as previously described and OARSI score determined blindly for each specimen.

Human Samples

Paraffin sections of human cartilage from a bone excised at the time of joint replacement, were supplied by the BioRepository Center of the NYU Langone Medical Center. The cartilage was harvested from OA patients undergoing total knee replacement surgery and provided without identifiers other than gender and age. Following incubation with primary antibodies slides were incubated with anti-rabbit FITC and anti-mouse TRITC, and imaged under fluorescence microscopy.

Mouse Bone Evaluation by µCT

After sacrifice right hind limbs from mice were disarticulated and used for morphology and measurement of bone features by µCT. After fixation in 70% ethanol, femora and tibiae of each sample were scanned with a SKYSCAN-1172 instrument and analyzed for subchondral bone density. Briefly, serial 12.5-µm tomographic images were acquired at the condition of 70 kV and 113 mA. Constant thresholds (200) were performed in binary images to segment bone from bone marrow. 2D and 3D images were obtained and the region of interest (ROI) in subchondral bone was defined as a sclerotic area contouring from the bone surface above the growth plate.

µCT Cartilage Examination

After washing with PBS, rat knees (femoral and tibial surfaces, n=3 for each group) were incubated in PBS containing the ionic contrast agent Hexabrixr (40% v/v) for 6 hours. All joints were evaluated in a (16 mm) scanning tube providing a volex size of 10.5 µm and scanned at 55 kV, 181 µA, 110 minutes of acquisition time. During scanning the samples were wrapped in paper soaked in PBS to avoid dehydration.

Mouse Primary Chondrocyte Extraction and Culture

Articular chondrocytes were obtained from C57BL/6 WT or A2AKO newborn mice following a protocol previously described (Thirion et al., Methods in Molecular Medicine 2004; 100:1-14), Primary chondrocytes (80% confluence) were starved for 5h. Cells were treated for 24h with mouse recombinant IL-1β (5 ng/ml) in DMEM containing 10% FBS and 1% Penicillin-Steptomycin. For intracellular ATP assay, cells were collected and lysed with RIPA buffer containing proteases and phosphatase inhibitors. For extracellular ATP and adenosine assays, complete media was replaced with DMEM without FBS and samples were collected after 10 minutes. ATP was assayed using a bioluminescent ATP determination kit following the manufacturer's instructions. Adenosine was extracted and tested by HPLC as previously described. ATP and adenosine data were normalized following protein quantification.

Protein Extraction and Western Blotting Assay

After cell treatments, the total protein extracts were collected and stored at −80° C. Total protein fractions were quantified using the BCA kit (Thermo Scientific). Western blotting was performed by electrophoresing 10 μg/ml protein through a 10% polyacrylamide gel followed by transfer of proteins to nitrocellulose membranes. Nitrocellulose membranes were incubated overnight at 4° C. with the specific primary antibody (1:1000), and after washing, incubated with goat anti-rabbit IRDye 800 CW and goat anti-mouse IRDye 680 RD (1:5000). Membranes were scanned with Li-cor Odyssey equipment and the intensities of the protein bands were quantified by densitometric analysis using Image Studio 2.0 38 software.

Reverse Transcription and Real Time PCR

RNA extraction was performed from mouse primary chondrocytes using RNeasy Mini Kit (Qiagen, Invitrogen) and QIAshredder colums (Qiagen, Invitrogen), following the manufacturer's protocol. RNA reverse transcription was performed using the MuLV Reverse Transcriptase PCR Kit (Applied Biosystems). After RNA reverse transcription to cDNA, real time PCR reactions were performed for a relative quantification of COL10a1 (forward: 5'-TTCTGCTGCTAATGTTCTTGACC-3' (SEQ ID NO: 1); reverse: 5'-GGGATGAAGTATTGTGTCTTGGG-3' (SEQ ID NO: 2)), Mmp-13 (forward: 5'-TGTTTGCAGAGCACTACTT-GAA-3' (SEQ ID NO: 3); reverse: 5'-CAGTCAC-CTCTAAGCCAAAGAAA-3' (SEQ ID NO: 4)), ENTPD1 (forward: 5'-ACAAGGGCTGCGAGATAAGA-3' (SEQ ID NO: 5); reverse: 5'-CCACCCAGACCTGTTGACTT-3' (SEQ ID NO: 6)), NT5E (forward: CAAATCCCACA-CAACCACTG-3' (SEQ ID NO: 7); reverse: 5'-TGCT-CACTTGGTCACAGGAC-3' (SEQ ID NO: 8)), PANX1 (forward: 5'-CCACCGAGCCCAAGTTCAA-3' (SEQ ID NO: 9); reverse: 5'-CCGGGTTGTTGAGTGTTACAG-3' (SEQ ID NO: 10)), SLC29A1 (forward: 5'-CCAGTGGT-TCTGAGCTGTCA-3' (SEQ ID NO: 11); reverse: 5'-CT-GTTGGTGGGTGGAGAGTT-3' (SEQ ID NO: 12)), SLC29A2 (forward: 5'-GCTGGGTACCATGCCTTCTA-3' (SEQ ID NO: 13); reverse: 5'-CCACACAGGGTGTGAT-GAAG-3' (SEQ ID NO: 14)) and ANKH (forward: 5'-CAAGAGAGACAGGGCCAAAG-3' (SEQ ID NO: 15); reverse: 5'-AAGGCAGCGAGATACAGGAA-3' (SEQ ID NO: 16)) performed on a Stratagene Mx3005P (Agilent Technologies, CA, USA) with Brilliant SYBR Green Kit QPCR. Master Mix (Stratagene, Agilent Technologies, CA, USA), according to the manufacturer's protocol.

Immunofluorescence

Cells were plated in 8-well chamber slides and, after the appropriate treatments, were washed with cold PBS and fixed with cold methanol (10 minutes). Cells were permeabilized using a solution of PBS containing Triton 0.25% for 10 minutes. After 3 washes for 5 minutes each, a blocking solution (FBS 5%, BSA 1% in PBST) was added to the cells for 1 hour. Cells were incubated with primary antibody against collagen-X, MMP-13 or CD73 antibody overnight. Cells were washed 3 times for 5 minutes each with PBS and incubated with the secondary antibody FITC conjugate (1:200 in PBST) for 1 hour and with 0.5 ug/ml of TRIC-labelled Phalloidin for 30 minutes. After 3 washes of 5 minutes each, a cover slide was applied to the slide with a mounting media containing DAN. Immunofluorescence was revealed by the Nikon Eclipse Ni fluorescence compound microscope.

Data Analysis

μCT analysis of bone and cartilage volume was performed using CTvox software to reconstruct 2D and 3D images and to calculate various bone characteristics. Amira software (FEI, Oregon-USA) was used to reconstruct mice and rat joints from μCT data based on differential density of bone and Hexabrix-treated cartilage. Statistical significance for differences between groups was determined using Student's T-test, two-way or one-way ANOVA, as appropriate, using GraphPad software (GraphPad, San Diego, Calif.). If the overall differences were significant ($F<0.05$) then differences between groups were analyzed by Bonferroni post-hoc testing.

Results

Mobility of A2ARKO Mice

Figure 5A:
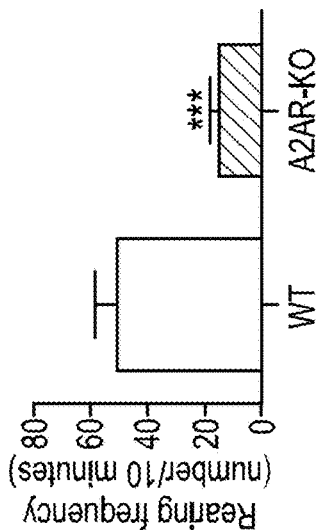
FIG. 5A, B, C, D, E, F provides the results of open field and rotarod tests that were carried out in 25-week old WT and A2ARKO mice (n=5 for each group) and the digital record analyzed, as described in Materials and Methods of Example 5. The mean (+SEM) values obtained during each 10 minute interval for distance moved, immobility time, rearing frequency, velocity of motion and time spent in the border and the latency to fall in the rotarod test are shown. Student T test or one-way ANOVA followed by Bonferroni post hoc test, as appropriate (*$p<0.05$, $p<0.01$, *$p<0.001$ vs WT).

Although the mobility of A2ARKO mice appeared to be limited, it was confirmed that deletion of A2AR leads to loss of mobility by subjecting WT and A2ARKO mice to an open field test to quantitate movement over time. The A2ARKO mice moved a shorter distance than WT mice (FIG. 5A, A2ARKO=664±123 cm vs WT 1404±129 cm; $p<0.001$), moved less quickly (velocity for A2ARKO=1.11±0.21 cm/sec vs WT 2.34±0.22 cm/sec; $p<0.001$) with increased time spent in the border of the cage (A2ARKO=575.5±7.7 sec vs WT=370.2±45.6 cm/sec; $p<0.001$) and immobile (A2ARKO=530.8±11.5 sec vs WT 442.3±15.4 sec; $p<0.001$). The frequency of rearing, a normal mouse exploratory behavior (measured in the first 10 minutes of the field test), was also reduced in A2ARKO mice (15±4 times/10 minutes, $p<0.0001$) compared to WT mice (51±7 times/10 minutes). The capacity of the A2ARKO mice to run on the rotarod apparatus with a constant acceleration was also reduced compared to the WT mice (A2ARKO=86±11 sec vs WT=145±22 sec, $p<0.01$).

μCT Analysis of Knee Joints in A2ARKO and WT Mice

Figure 5B:
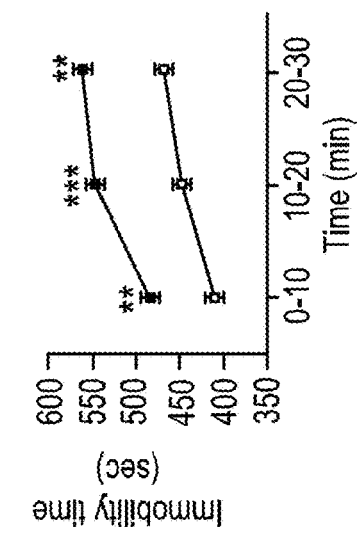
FIG. 5(A,B,C,D,E,F,G,H,I) depicts osteoarthritis in A2ARKO mice.
FIG. 5G, H, I provides immunohistologic staining for Collagen X and MMP-13 in a representative section of tibia from a WT and A2ARKO mouse (12 week old mice, original magnification 400×). Sections from the same mice stained with Safranin O and hematoxylin and eosin (H&E) are shown in the right-hand panels (Original Magnification 100×). In the lower panel (right) is plotted the OARSI scores obtained on safranin-O-stained knees, as described in Materials and Methods of Example 5. Each data point represents the mean (+SEM) of the blinded scores obtained on 5 different mice. On the left bottom of the figure are representative images from µCT of a 12-week old WT and A2ARKO mouse. The box highlights subchondral sclerosis of bone in the A2ARKO mouse.
Figure 5C:
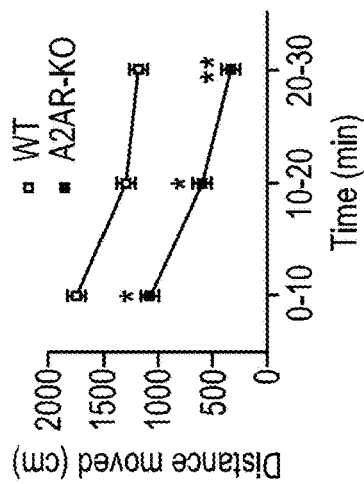
Figure 5D:
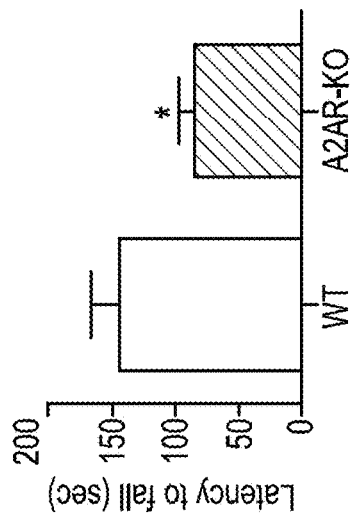
Figure 5E:
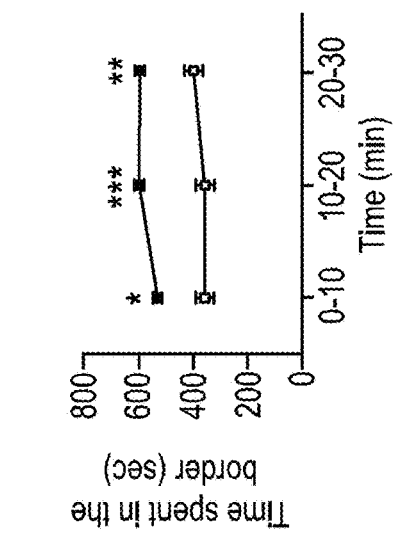
Figure 5F:
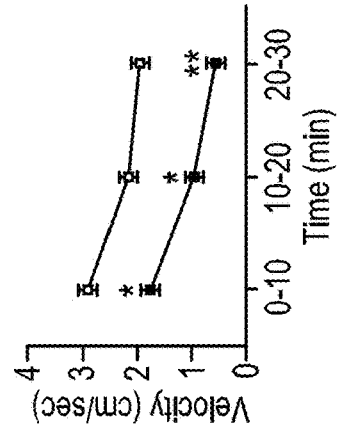
Figure 5G:
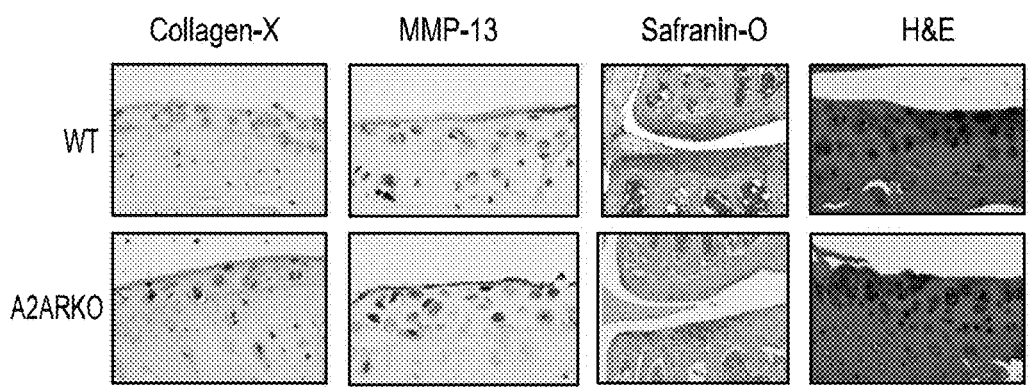
Figure 5H:
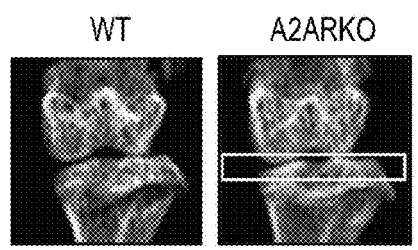
Figure 5I:
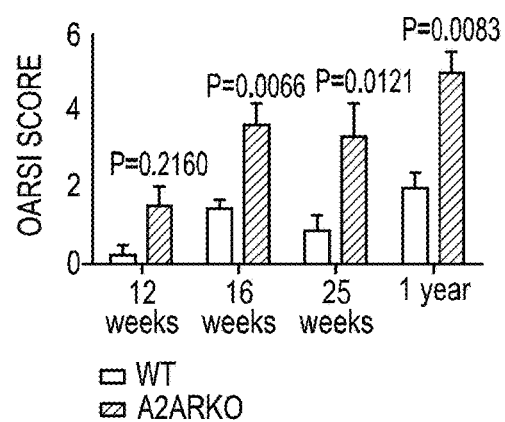
Figure 6A:
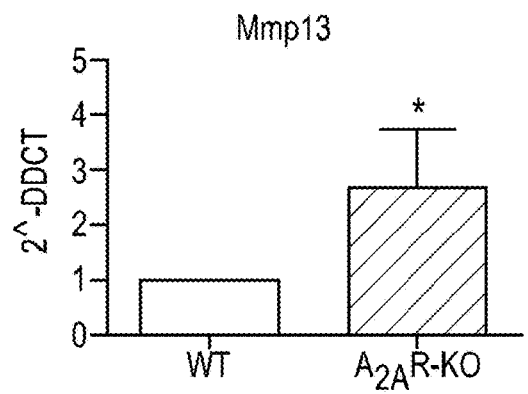
FIG. 6A, 6B provides the results when primary chondrocytes were isolated from neonatal WT and A2AR-KO mice. RNA was isolated, reverse transcribed and analyzed by real time PCR. Expression levels normalized to GAPDH are shown for Mmp13 and Col10a1 levels when compared to levels in WT cells.
Figure 6B:
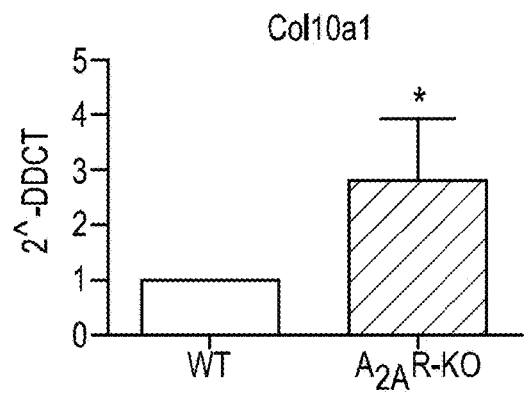
Figure 6C:
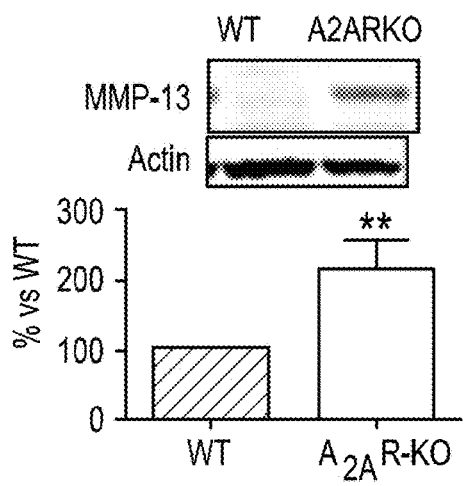
FIG. 6C, 6D provides representative Western blots for MMP-13 and collagen X, and quantification of protein bands in the bar graphs below (n=4).
Figure 6D:
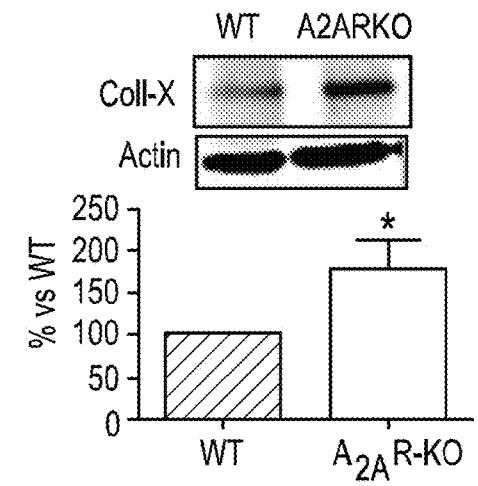
Figure 6E:
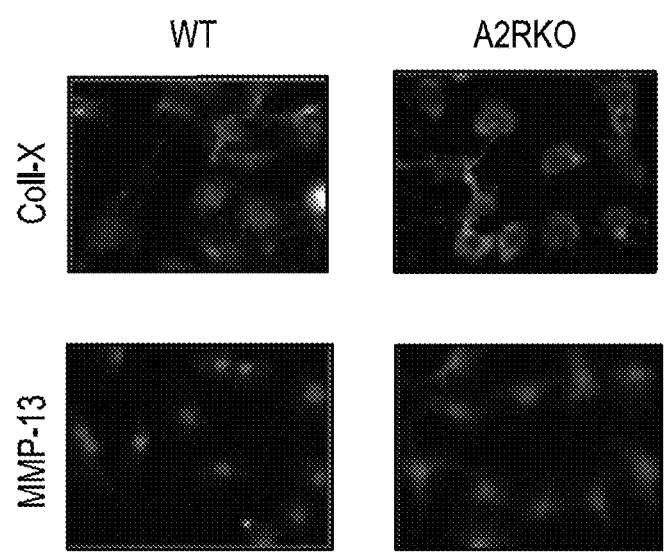
FIG. 6E demonstrates that staining of cell layers shows increases in MMP-13 and collagen X in the A2ARKO chondrocytes compare to the WT. (n=4; data are represented as means±SEM. *, P<0.05; **, P<0.01 vs WT).

Because one potential cause for the difficulty of the A2ARKO mice in mobility, holding food and breeding could be the development of arthritis, the knees of A2ARKO mice were examined by μCT. Three dimensional reconstruction of μCT images demonstrated subchondral bony sclerosis and cartilage subsidence in the tibial heads of 8-, 12-, 26- and 52-week old A2AKO mice (FIG. 5B). Moreover, in the same A2ARKO mice there were osteophytes that increased in size as the animals aged. No bony or cartilaginous changes were observed in WT mice (FIG. 5B). The bone and cartilage changes observed were similar in male and female A2ARKO mice.

Histopathologic Changes in Cartilage of A2AR KO Mice

Figure 10A:
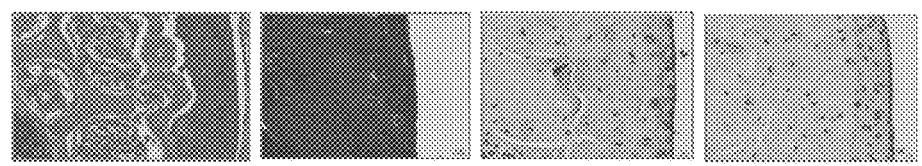
FIG. 10(A,B) provides representative photomicrographs of histological sections of the distal femoral condyles in WT and A2AR-KO mice at 16 weeks of age. Periodic acid Schiff (PAS) staining and Trichrome staining show progressive reduction of glycogen (lighter staining) and collagen (darker staining) in the matrix of cartilage components in A2ARKO (FIG. 10B) mice as compared to WT mice (FIG. 10A). On the right are representative photomicrographs of the distal femoral condyles in WT and A2AR-KO mice at 16 weeks analyzed for osteopontin and fibronectin by immunohistochemistry, as described in Example 5.
Figure 10B:
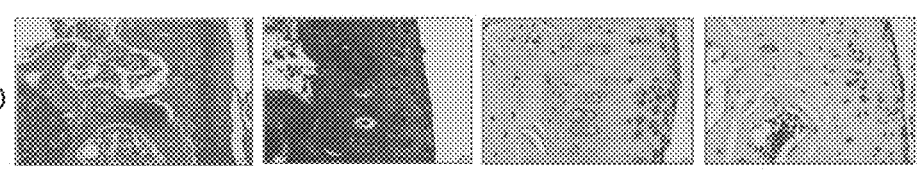

The radiologic appearance of the joints obtained by μCT resembled changes seen in OA; to confirm that the radiologic changes reflected OA in the joints of the A2ARKO mice, histologic sections of the knees of these mice were examined. Examination of H&E-stained knees revealed progressive reduction in cartilage thickness in A2ARKO mice compared to WT mice; these changes were detectable as early as 12 weeks of age (FIG. 5B). Over time there was increased fibrillation and thinning of cartilage as well, with increased subchondral bone and osteophytes. The chondrocytes present in the cartilage of the A2ARKO mice were increasingly disordered over time, as well. There was significantly less glycosaminoglycan staining in the cartilage of A2AR KO mice by safranin O staining (FIG. 5B) and PAS and trichrome stains further demonstrated loss of sulfated proteoglycans and collagen in the cartilage matrix (FIG. 10). These changes were detectable as early as 12 weeks of age. Immunohistochemical staining showed increased MMP-13-positive and collagen X (FIG. 5B), osteopontin- and fibronectin-positive cells in cartilage matrix of the A2AR-KO mice starting as early as 12 weeks of age (FIG. 10). Finally, a composite score for osteoarthritic changes (OARSI score) showed marked differences between A2ARKO and WT mice, and the differences increased over time. Increased OARSI scores were first detectable at 12 weeks of age. Both male and female A2ARKO mice were affected by OA although the changes were milder in females than males (e.g. OARSI score at 1 year 4.8±0.6 vs 20 3.2±0.2, males vs females, respectively, p<0.05, n=5 for each).

Figure 12:
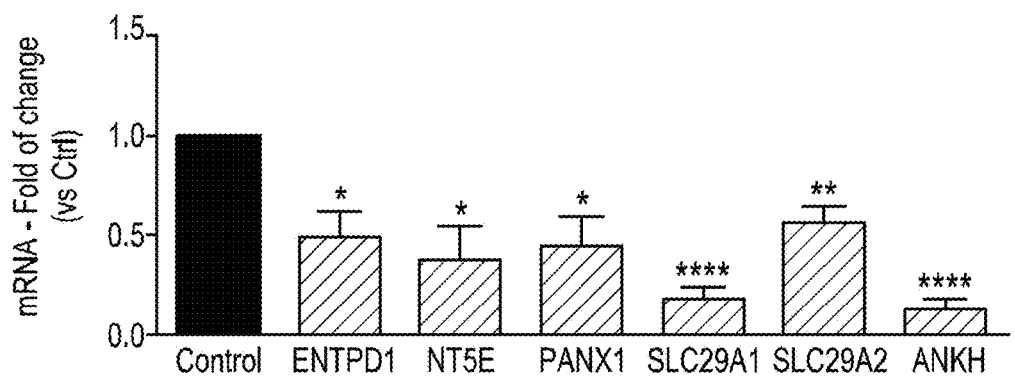
FIG. 12 demonstrates that IL-1β treatment decreases expression of mRNA for enzymes and transporters involved in maintaining adenosine levels in the extracellular space. Murine chondrocytes were isolated and treated for 24 hours with IL-1β (5 ng/ml) before isolation of RNA, reverse transcription and quantitation by RT-PCR. There are significant decreases in ENTPD1, NTSE, PANX1, SLC29A1, SLC29A2 and ANKH mRNA. (n=4; data are represented as mean±SEM. *, p<0.05; , p<0.01; **, p<0.001 vs. Control).
Figure 13:
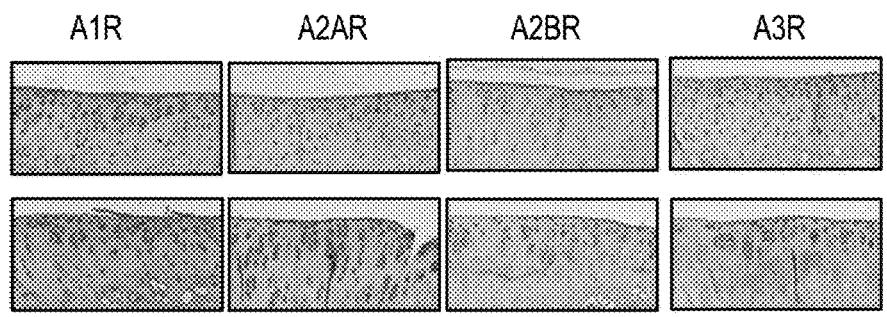
FIG. 13 demonstrates that A2AR expression increase in chondrocytes of OA rats. Representative photomicrographs of adenosine receptor immunostaining of chondrocytes. A1R, A2AR, A2BR and A3R expressed in rat articular cartilage are provided. A2AR expression increases in chondrocytes of OA rats.

Deletion of A2AR Increases Neonatal Chondrocyte Expression of MMP13 and Col10a1 and IL-1β Treatment Contribute to Adenosine Availability Reduction In contrast to normal resting chondrocytes, chondrocytes from osteoarthritic cartilage express markers of hypertrophy, e.g. col10a1, in addition to mediators that participate in the destruction of cartilage, e.g. matrix metalloproteases like MMP13. As expected, chondrocytes isolated from the cartilage of neonatal WT mice do not express col10a1 or MMP13 mRNA or protein (FIG. 6(A,B,C)). In contrast, chondrocytes from neonatal A2ARKO mice express both of these markers of OA (FIG. 6(A,B,C)). These findings demonstrate that even shortly after birth chondrocytes from A2ARKO mice are already dysregulated and the changes likely contribute to the OA phenotype observed in the A2ARKO mice. IL-1β decrease adenosine availability since treatment of murine chondrocytes with IL-1β (5 ng/ml for 24 hours) significantly decrease message of CD39 (ENTPD1, p<0.05), CD73 (NT5E, p<0.05), Pannexin 1 (PANX1, p<0.05), Nucleoside transporter 1 and 2 (respectively SLC29A1, p<0.0001 and SLC29A2, p<0.01) and inorganic pyrophosphate transporter ANK (ANKH, p<0.0001; n=4 for each experiment performed in duplicate; FIG. 12).

A2AR Expression in Human OA

To determine whether loss of A2AR plays a role in human OA A2AR expression on chondrocytes in osteoarthritic cartilage were examined. A2AR were upregulated in the chondrocytes of patients with OA and appeared to colocalize with expression of MMP13, a reflection of OA changes in chondrocytes (FIG. 11(A,B,C)). This change was not surprising as it has been demonstrated that there is upregulation of both A2AR receptor expression and function following exposure to inflammatory stimuli (IL-1β and TNFα) which acts as a feedback regulator of inflammation in both murine and human cells (Khoa et al., *J Immunol* 2001; 167:4026-4032; Nguyen et al., *J Immunol* 2003; 171:3991-3998; Bshesh et al., *Journal of Leukocyte Biology.* 2002; 72:1027-1036; Elson et al., *Genes and Immunity* 2003; 14:147-153; Khoa et al., *Molecular Pharmacology* 2006; 69:1311-1319; Firestein et al., *Journal of Immunology* 1990; 144:3347-3353). One explanation for the difference between A2AR expression in human and murine OA cartilage is that the findings in A2ARKO mice do not reflect OA development in humans. Alternatively, the disparity between human and murine OA cartilage suggests that despite overexpression of A2AR there is diminished ligand for A2AR and resulting loss of A2AR function leading to development of OA.

Adenosine and ATP Release Decrease After Il-1β Treatment

Figure 7A:
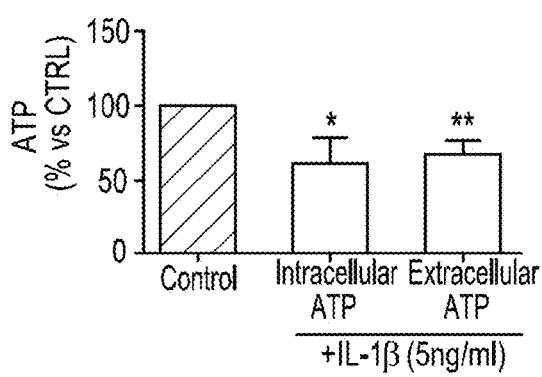
FIGS. 7A and 7B demonstrate that treatment of primary murine chondrocytes with IL-1β (5 ng/ml for 24 hours) decreases the intracellular ATP content and the concentration of ATP in the supernatant medium (7A) and the concentration of adenosine in the supernatant medium (7B). Data are expressed as mean±SEM of experiments performed in duplicate for the adenosine determination and experiments performed in duplicate for the ATP assay. Student's T-test was performed; *p<0.05, **p<0.01).
Figure 7B:
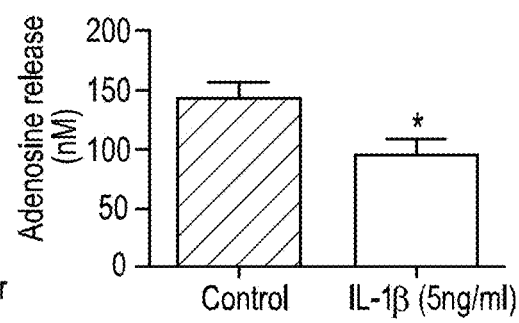

To test the hypothesis that OA chondrocytes release less adenosine and its precursor, ATP, adenosine and ATP release were quantitated from cultured neonatal murine chondrocytes and determined whether IL-1β treatment altered this release. Primary murine chondrocytes release ATP into the extracellular space and that adenosine is present in supernates of cultured chondrocytes (FIG. 9(A,B,C,D)). Treatment of primary murine chondrocytes with IL-1β (5 ng/ml) for 24 hours reduced the level of intracellular ATP (to 61±9% of control, p<0.05, FIG. 7A) and the ATP released into the supernates of cultured chondrocytes (to 66±3% of control, p<0.001, FIG. 7A). Similarly, IL-1β treatment reduced the adenosine concentration in the supernates of cultured chondrocytes to 65% of control (Control=143±14 nM vs IL-1β=94±14 nM, p<0.02, n=9, FIG. 7B).

To understand how IL-1β treatment reduces ATP and adenosine release, the effect of IL-1β on expression of ATP transporters (ANKH, pannexin1) was examined, the ectoenzymes involved in conversion of ATP to adenosine (ectonucleotide triphosphate dephorphorylase, ENTPD1 and ecto-5' nucleotidase, NT5E) and the transporters responsible for adenosine transport to and from the extracellular space (nucleoside transporters 1 and 2, SLC29A1 and SLC29A2, respectively). In addition to reducing intracellular levels of ATP, treatment of murine chondrocytes with IL-1β (5 ng/ml for 24 hours) significantly reduced expression of message for all of these molecules (n=4 for each experiment, FIG. 12).

Figure 7C:
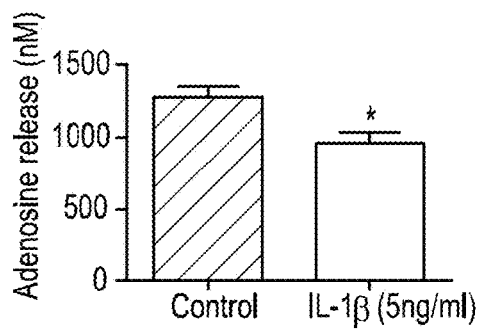
FIG. 7C, D provides adenosine levels in supernatants of control and IL-1β-treated rat tibial plateau explants (left) and following mechanical loading of the tibial plateau explants (right, data were analyzed for statistical significance by two-way ANOVA followed by Bonferroni post-hoc test *p<0.05). The data are expressed as the mean±SEM of 5 experiments for adenosine release and the adenosine concentration was normalized to the weight of the tibial explant.
Figure 7D:
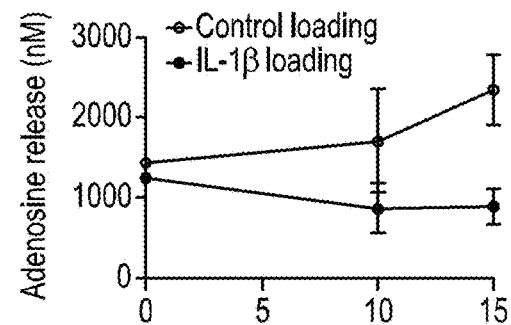
FIG. 7(A,B,C,D,E) represents that intracellular ATP and spontaneous adenosine and ATP release from primary cultured neonatal chondrocytes decrease after treatment with IL-1β.
FIG. 7E represents ATP concentration in supernates of tibial explants, measured as described in Example 5. Each point represents the mean±SEM of 3 separate determinations.
Figure 7E:
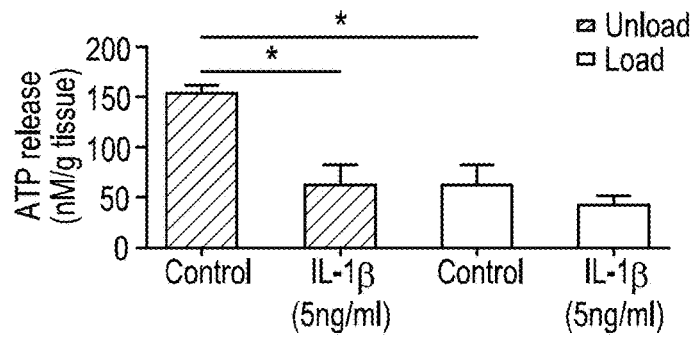

Because chondrocytes cultured as a monolayer may not behave like chondrocytes embedded within a matrix, whether there was a similar reduction in ATP and adenosine release from rat chondrocyte explants was examined. Both ATP and adenosine (FIGS. 7A and 7B) are released from rat tibial plateau explants and treatment of these cartilage explants with IL-1β reduced adenosine release from cells. The effect of weight loading, within the physiologic range, on ATP and adenosine release from rat cartilage explants was determined and found that there was a marked increase in adenosine release that was abrogated by pre-treatment with IL-10 (1657±177 nM vs 960±57 nM, respectively, n=5; FIG. 7C). After loading of explants there was no detectable change in ATP levels in supernates IL-1β-treated explants from control although there was nearly a 2-fold increase in the adenosine concentration (FIG. 7D). Most likely the increase in adenosine concentration reflects rapid conversion of ATP to adenosine as the cartilage is loaded.

Reduced Capacity to Generate Extracellular Adenosine Leads to OA

Figure 8A:
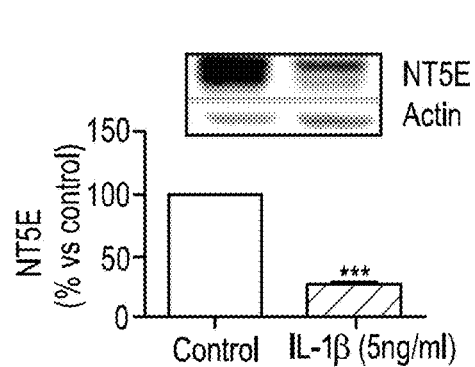
FIG. 8A, B demonstrates that 24 hours treatment with IL-1β decreases NT5E expression in the total protein content and NT5E membrane expression on the cell membrane. Representative NT5E western blot and protein quantification is shown on the graph on the left side of the figure and on the right are shown representative immunofluorescence photomicrographs of NT5E (green fluorescence) and phalloidin staining (red fluorescence).

Multiple transporters and enzymes are involved in the release of ATP from cells and conversion of extracellular adenine nucleotides to adenosine. ANKH and pannexin1 all transport ATP out of the cell (Rosenthal et al., *Arthritis Research & Therapy* 2013; 15:R154; Praetorius et al., *Purinergic Signalling* 2009; 5:433-446), and while multiple phosphatases can convert ATP to adenine nucleotides and adenosine, ectoenzymes on the cell surface (ENTPD1 and NT5E) may play a critical role in the generation of adenosine available for ligation of adenosine receptors. Other membrane proteins transport adenosine into and out of the cell (nucleoside transporters 1 and 2, 11 SLC29A1 and SLC29A2, respectively). Treatment of murine chondrocytes with IL-10 (5 ng/ml for 24 hours) significantly reduced expression of message for all of these molecules (n=4 for each, FIG. 12). Moreover the treatment of murine chondrocytes with IL-10 (5 ng/ml) decreased NT5E protein expression and its localization on chondrocyte surface (FIG. 8A).

Figure 8B:
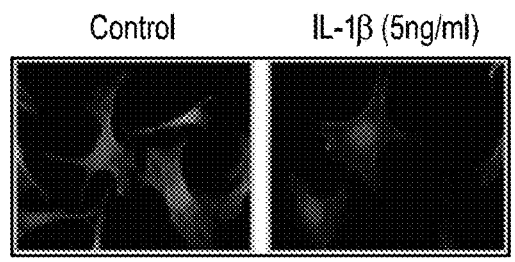
FIG. 8(A,B,C) demonstrates that NT5E decreases after IL-1β treatment and NT5E KO mice manifest mild osteoarthritis.
FIG. 8C shows representative images of knees from 1-year old NT5E KO mice with cartilage fraying, minimal loss of proteoglycan and increased MMP-13 expression by immunohistochemistry. The black arrow in the safranin-O-stained section indicates an osteophyte.
Figure 8C:
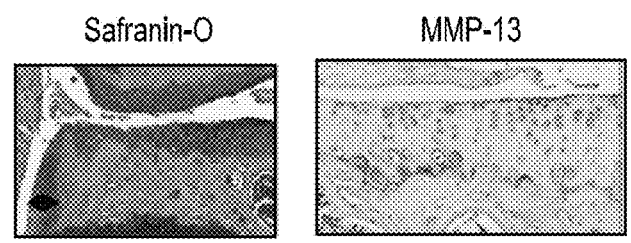

Mice lacking ANKH develop severe arthritis at an early age and the joint destruction bears many of the hallmarks of OA, such as osteophytes (Ho et al., *Science* 2000; 289:265-270). Mice lacking ENTPD1 have no changes in their joints (Not shown) but mice lacking NTSE develop mild osteoarthritic changes in their joints (OARSI score=1.5±0.84 vs WT=0.5±0.15) with mild articular cartilage fibrillation, loss of cartilage proteoglycan and osteophytes (FIG. 8B). Interestingly, humans lacking NT5E develop severe arterial calcification and have been noted to have periarticular calcification and arthritis as 21 well (St Hilaire et al., *The New England Journal of Medicine* 2011; 364:432-442; Ichikawa et al., *Journal of Clinical Rheumatology: practical reports on rheumatic & musculoskeletal diseases* 2015; 21:216-220). These results are consistent with the hypothesis that diminished capacity to generate extracellular adenosine contributes to the pathogenesis of OA.

Liposomal Adenosine Protects From OA Progression in PTOA Rats

Figure 9B:
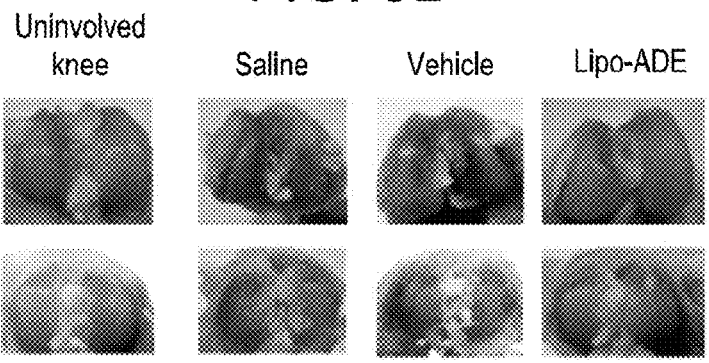
FIG. 9B, C, D provides representative photographs of the gross appearance of the knees of the rats at the time of sacrifice (top row femur, bottom row tibia) and on the bottom knee size measured with a caliper immediately prior to injection.
Figure 9C:
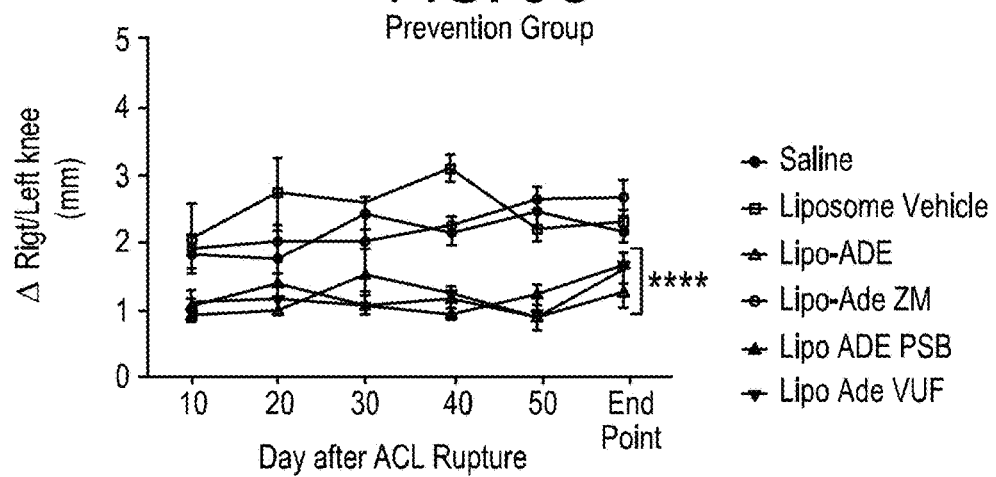
FIG. 9(A,B,C,D,E,F,G,H,I,J,K,L) demonstrates that injection of liposomal adenosine prevents and treats OA in a rat model of post-traumatic OA via A2AR ligation.
FIG. 9A shows the experimental design with anterior cruciate ligament disruption on day 0 followed by injection of liposomal adenosine at the indicated times.
FIG. 9E, F provides representative µCT images of hexabrix-imaged cartilage (Top row femur, Bottom row, tibia). The cartilage is lighter in this image and underlying bone is darker. In the panel beneath is shown the mean (+SEM) volume of cartilage present in the affected knee expressed as the percentage of the volume of cartilage in the unaffected knee. S, saline-injected; L, empty liposome-injected; 9A, adenosine-liposome injected.
FIG. 9G, H, I shows representative safranin-O-stained sections and immunohistologic sections for MMP-13 expression in rat tibial plateaus following ACL rupture. Graphs show the OARSI scores of the knees of the rats studied here.
FIG. 9J, K, L provides representative gross photograph and photomicrographs of rat knee injected with liposome formulation containing adenosine plus ZM241385 and respective safranin-O staining and MMP-13 immuhohistochemistry. Graphs show the OARSI scores for rat knees treated with adenosine plus adenosine receptor antagonists. Data are expressed as mean±SEM of 5-6 animals for each group and data were analyzed for statistical significance by one-way ANOVA followed by Bonferroni post-hoc test of differences among various treatments (*p<0.05; p<0.01, *p<0.001, ****p<0.0001).
Figure 9D:
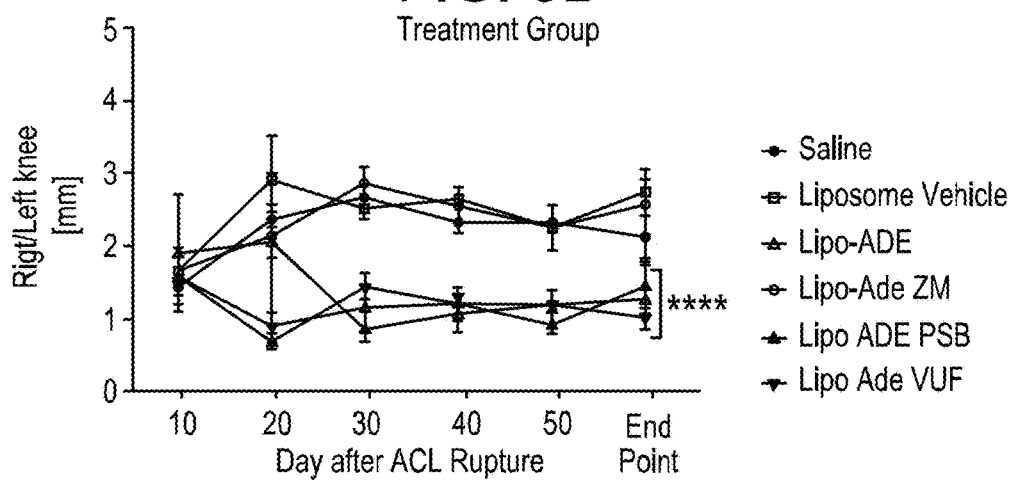
Figure 9E:
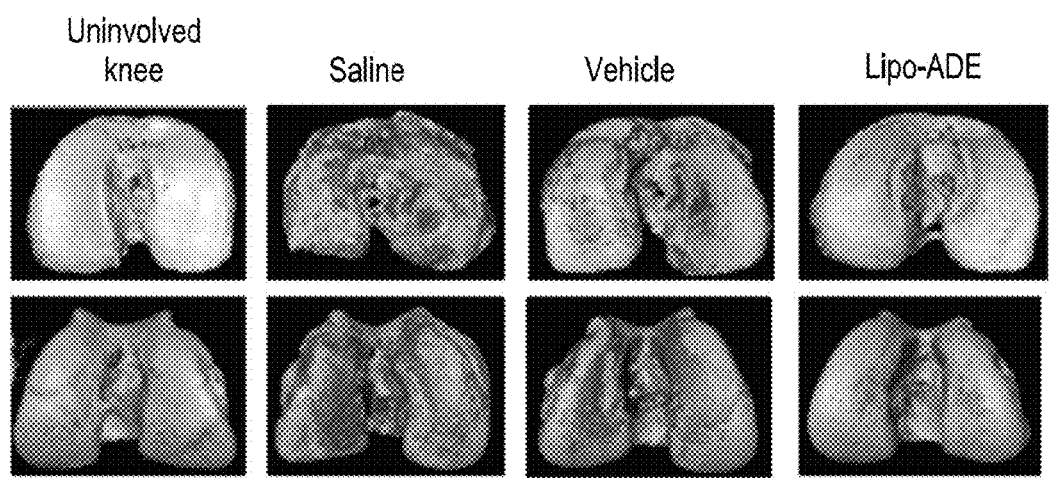
Figure 9F:
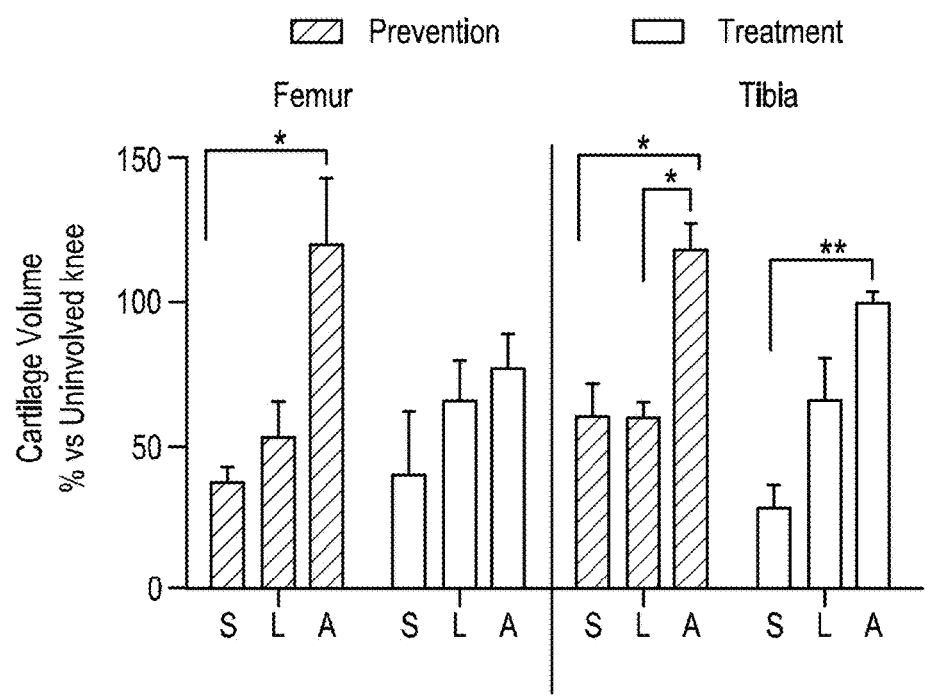
Figure 9G:
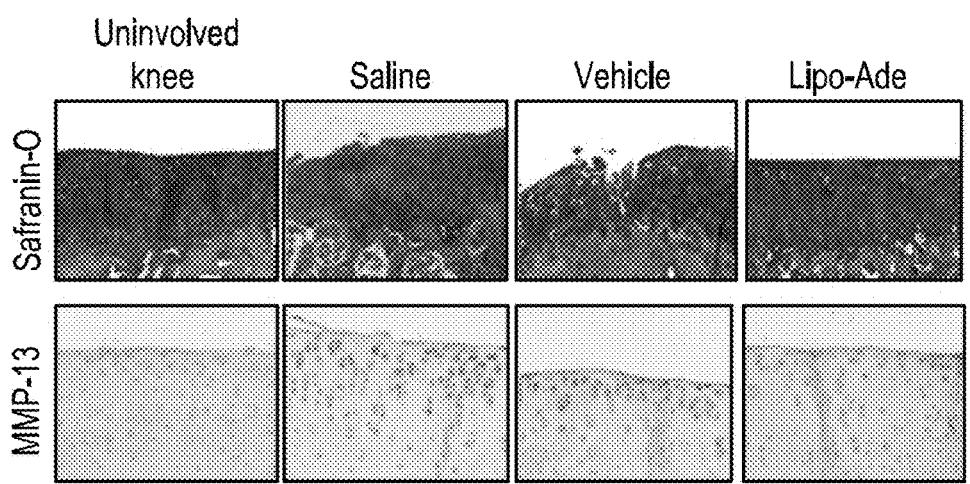
Figure 9H:
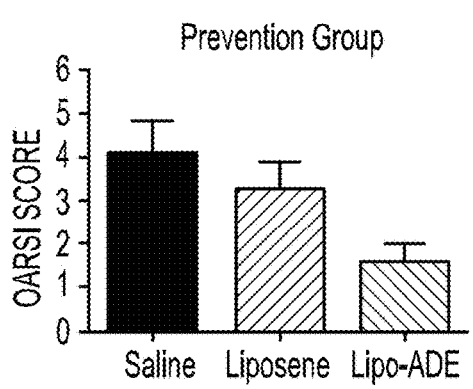
Figure 9I:
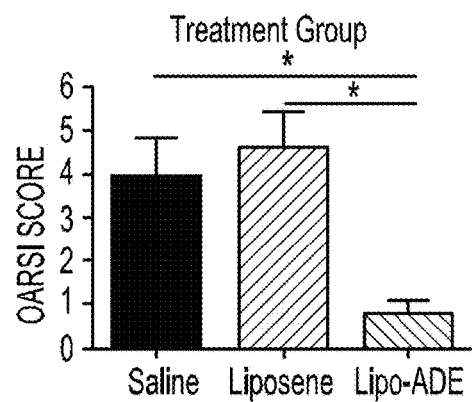
Figure 9J:
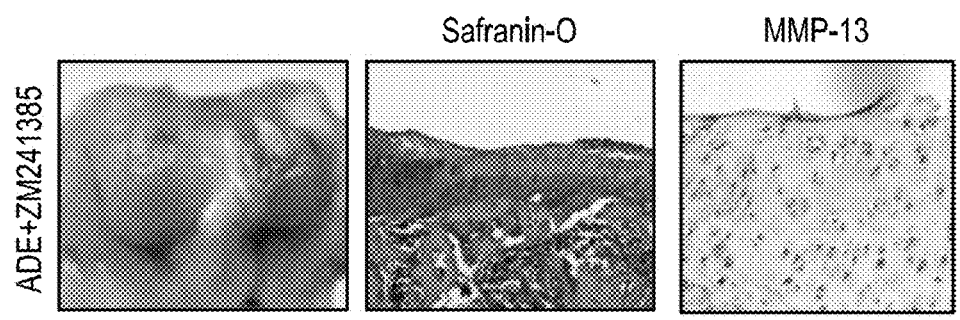
Figure 9K:
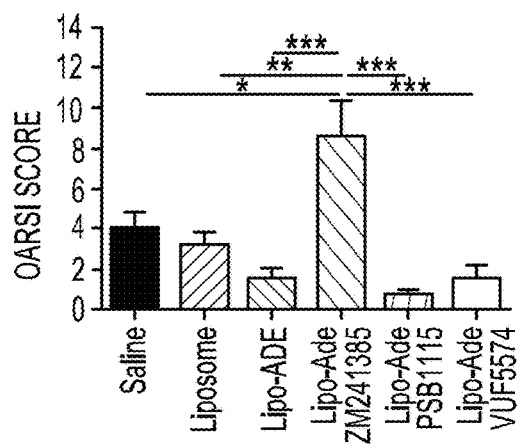
Figure 9L:
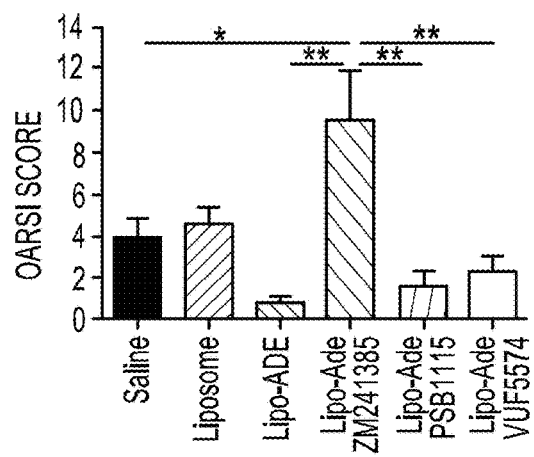

If diminished adenosine levels and A2AR stimulation play a role in the pathogenesis of OA then adenosine repletion might represent one approach to the treatment or prevention of OA. Because adenosine itself has an extremely short half-life (measured in seconds) in blood and other bodily fluids due to the presence of enzymes that degrade adenosine as well as cellular uptake of adenosine. Adenosine was formulated in liposomes to prolong the half-life of adenosine and the effect of liposomal adenosine preparations on the development of OA was tested in a rat model of post-traumatic OA (Ichikawa et al., *Journal of Clinical Rheumatology: practical reports on rheumatic & musculoskeletal diseases* 2015; 21:216-220; Deussen et al., *American Journal of Physiology* 1993; 264:H692-700). Liposomal adenosine, saline or empty liposomes were injected into the affected joint at the time of injury (prevention) or beginning one week later (treatment) and continued in both groups every 10 days for a total of 6 or 5 joint injections, respectively (FIG. 9A). Of note, injection of liposomal adenosine almost completely prevented joint swelling in the prevention group and markedly reduced joint swelling in the treatment group over the course of the treatment (FIG. 9B). There was almost complete destruction of the affected articular cartilage in the saline- and liposome-treated rats whereas the liposomal adenosine-treated rats were almost completely protected from cartilage destruction and microCT of hexabrix-stained cartilage confirms these effects (FIG. 9C). Consistent with the gross and radiologic findings, histologic examination of the joints demonstrated almost complete protection of the joints by liposomal adenosine but not by injections of either saline or empty liposomes (FIG. 9D). In the prevention group treatment with intra-articular injections of saline, empty liposomes and liposomal adenosine resulted in OARSI scores of 4.1±0.8, 3.3±0.6 and 1.6±0.4, respectively (FIG. 9D) and in the treatment group the corresponding OARSI scores were 3.9±0.9, 4.5±0.8 and 0.8±0.3, respectively. Thus, intra-articular administration of liposomal adenosine nearly completely prevented the development of OA.

The Protective Effect of Liposomal Adenosine is Mediated by Ligation of A2AR

There are multiple adenosine receptors the actions of which can be differentiated by use of appropriate pharmacologic antagonists and agonists. To determine which adenosine receptors are involved in this mechanism, rats were treated with liposomal adenosine plus either an A2AR antagonist (ZM241385), A2BR antagonist (PSB1115) or A3R antagonist (VUF5574.). The co-administration of the A2AR antagonist, but not either the A2BR or A3R antagonist, reversed the effect of liposomal adenosine injections on joint swelling, cartilage degradation or chondrocyte expression of MMP-13. Moreover the OARSI scores of knees from mice treated with liposomal adenosine in the presence of the A2AR antagonist (8.7±1.8 in the prevention group and 9.6±2.3 in the treatment group) were markedly increased compared to those of the knees of rats co-administered either the A2BR (0.8±1.0 for the prevention group and 1.6±0.8 for the treatment group) or A3R antagonist (1.7±0.6 for the prevention group and 2.4±0.6 for the treatment group, 11 FIG. 9D). These results provide strong evidence that A2AR mediates the chondroprotective effects of intraarticular injection of liposomal adenosine.

The invention claimed is:

1. A method for treating or inhibiting the development of osteoarthritis in a subject having osteoarthritis, comprising administering to the subject via intraarticular injection a therapeutically effective amount of a composition comprising one or more agent selected from the group consisting of adenosine, an adenosine receptor $A_{2A}$ agonist, and ticagrelor, or an analog or derivative thereof, wherein the composition extends the biological activity of the agent.

2. The method of claim 1 wherein and the adenosine receptor $A_{2A}$ agonist is a selective adenosine receptor $A_{2A}$ agonist.

3. The method of claim 1 further comprising administering one or more other therapeutically effective compound or agent.

4. The method of claim 3 wherein the one or more other therapeutically effective compound or agent is selected from the group consisting of an anti-inflammatory compound, a bisphosphonate and a growth factor.

5. The method of claim 1 wherein the composition is injected into synovial fluid of a joint.

6. The method of claim 1 wherein the composition is effective to reduce or inhibit degeneration or damage to cartilage.

7. The method of claim 1 wherein the composition is a liposomal composition or comprises a liposome.

8. A method for stimulating or increasing cartilage production or formation in a subject comprising administering to the subject via intraarticular injection a therapeutically effective amount of a composition comprising one or more agent selected from the group consisting of adenosine, an adenosine receptor $A_{2A}$ agonist, and ticagrelor, or an analog or derivative thereof, wherein the composition extends the biological activity of the agent.

9. The method of claim 8 wherein and the adenosine receptor $A_{2A}$ agonist is a selective adenosine receptor $A_{2A}$ agonist.

10. The method of claim 8 further comprising administering one or more other therapeutically effective compound or agent.

11. The method of claim 10 wherein the one or more other therapeutically effective compound or agent is selected from the group consisting of an anti-inflammatory compound, a bisphosphonate and a growth factor.

12. The method of claim 8 wherein the composition is injected into synovial fluid of a joint.

13. The method of claim 8 wherein the composition is effective to reduce or inhibit degeneration or damage to cartilage.

14. The method of claim 8 wherein the composition is a liposomal composition or comprises a liposome.

15. The method for treating or inhibiting the development of osteoarthritis in a subject having osteoarthritis according to claim 1 wherein the composition contains a liposome or liposomal composition, a hyaluronate suspension, a microsphere, a nanofiber, a protein conjugate, or a nanoparticle.

16. The method for stimulating or increasing cartilage production or formation in a subject according to claim 8 wherein the composition contains a liposome or liposomal composition, a hyaluronate suspension, a microsphere, a nanofiber, a protein conjugate, or a nanoparticle.

17. A method for treating or inhibiting the development of osteoarthritis in a subject having osteoarthritis, comprising administering to the subject via intraarticular injection a therapeutically effective amount of a composition comprising one or more agent selected from the group consisting of adenosine and ticagrelor, or an analog or derivative thereof, wherein the composition extends the biological activity of the agent.

18. A method for treating or inhibiting the development of osteoarthritis in a subject having osteoarthritis according to claim 17, comprising administering to the subject via intraarticular injection a therapeutically effective amount of a composition comprising adenosine or an analog or derivative thereof, wherein the composition extends the biological activity of the adenosine.

19. A method for treating or inhibiting the development of osteoarthritis in a subject having osteoarthritis according to claim 17, comprising administering to the subject via intraarticular injection a therapeutically effective amount of a composition comprising ticagrelor or an analog or derivative thereof, wherein the composition extends the biological activity of the ticagrelor.

20. A method for stimulating or increasing cartilage production or formation in a subject comprising administering to the subject via intraarticular injection a therapeutically effective amount of a composition comprising one or more agent selected from the group consisting of adenosine and ticagrelor, or an analog or derivative thereof, wherein the composition extends the biological activity of the agent.

21. A method for stimulating or increasing cartilage production or formation in a subject according to claim 20 comprising administering to the subject via intraarticular injection a therapeutically effective amount of a composition comprising adenosine, or an analog or derivative thereof, wherein the composition extends the biological activity of the adenosine.

22. A method for stimulating or increasing cartilage production or formation in a subject according to claim 20 comprising administering to the subject via intraarticular injection a therapeutically effective amount of a composition comprising ticagrelor, or an analog or derivative thereof, wherein the composition extends the biological activity of the ticagrelor.

23. The method of claim 17 further comprising administering one or more other therapeutically effective compound or agent.

24. The method of claim 23 wherein the one or more other therapeutically effective compound or agent is selected from the group consisting of an anti-inflammatory compound, a bisphosphonate and a growth factor.

25. The method of claim 17 wherein the composition is injected into synovial fluid of a joint.

26. The method of claim 17 wherein the composition is effective to reduce or inhibit degeneration or damage to cartilage.

27. The method of claim 17 wherein the composition contains a liposome or liposomal composition, a hyaluronate suspension, a microsphere, a nanofiber, a protein conjugate, or a nanoparticle.

28. The method of claim 20 further comprising administering one or more other therapeutically effective compound or agent.

29. The method of claim 28 wherein the one or more other therapeutically effective compound or agent is selected from the group consisting of an anti-inflammatory compound, a bisphosphonate and a growth factor.

30. The method of claim 20 wherein the composition is injected into synovial fluid of a joint.

31. The method of claim 20 wherein the composition is effective to reduce or inhibit degeneration or damage to cartilage.

32. The method of claim 20 wherein the composition contains a liposome or liposomal composition, a hyaluronate suspension, a microsphere, a nanofiber, a protein conjugate, or a nanoparticle.

* * * * *

UNITED STATES PATENT AND TRADEMARK OFFICE
CERTIFICATE OF CORRECTION

| | |
|---|---|
| PATENT NO. | : 10,441,541 B2 |
| APPLICATION NO. | : 15/262372 |
| DATED | : October 15, 2019 |
| INVENTOR(S) | : Bruce N. Cronstein and Carmen Corciulol |

It is certified that error appears in the above-identified patent and that said Letters Patent is hereby corrected as shown below:

In the Specification

At Column 1, Line 4, add the following:
--This invention was made with government support under grant numbers R01 AR056672, R01 AR068593, and TR000038 awarded by the National Institutes of Health. The government has certain rights in the invention.--

Signed and Sealed this
Eighteenth Day of October, 2022

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 23
<212> TYPE: DNA
<213> ORGANISM: murine

<400> SEQUENCE: 1
ttctgctgct aatgttcttg acc             23

<210> SEQ ID NO 2
<211> LENGTH: 23
<212> TYPE: DNA
<213> ORGANISM: murine

<400> SEQUENCE: 2
gggatgaagt attgtgtctt ggg             23

<210> SEQ ID NO 3
<211> LENGTH: 22
<212> TYPE: DNA
<213> ORGANISM: murine

```
<400> SEQUENCE: 3
tgtttgcaga gcactacttg aa                                              22

<210> SEQ ID NO 4
<211> LENGTH: 23
<212> TYPE: DNA
<213> ORGANISM: murine

<400> SEQUENCE: 4
cagtcacctc taagccaaag aaa                                             23

<210> SEQ ID NO 5
<211> LENGTH: 20
<212> TYPE: DNA
<213> ORGANISM: murine

<400> SEQUENCE: 5
acaagggctg cgagataaga                                                 20

<210> SEQ ID NO 6
<211> LENGTH: 20
<212> TYPE: DNA
<213> ORGANISM: murine

<400> SEQUENCE: 6
ccacccagac ctgttgactt                                                 20

<210> SEQ ID NO 7
<211> LENGTH: 20
<212> TYPE: DNA
<213> ORGANISM: murine

<400> SEQUENCE: 7
caaatcccac acaaccactg                                                 20

<210> SEQ ID NO 8
<211> LENGTH: 20
<212> TYPE: DNA
<213> ORGANISM: murine

<400> SEQUENCE: 8
tgctcacttg gtcacaggac                                                 20

<210> SEQ ID NO 9
<211> LENGTH: 19
<212> TYPE: DNA
<213> ORGANISM: murine

<400> SEQUENCE: 9
ccaccgagcc caagttcaa                                                  19

<210> SEQ ID NO 10
<211> LENGTH: 21
<212> TYPE: DNA
<213> ORGANISM: murine

<400> SEQUENCE: 10
ccgggttgtt gagtgttaca g                                               21

<210> SEQ ID NO 11
<211> LENGTH: 21
<212> TYPE: DNA
```

```
<213> ORGANISM: murine

<400> SEQUENCE: 11
ccgggttgtt gagtgttaca g                                            21

<210> SEQ ID NO 12
<211> LENGTH: 20
<212> TYPE: DNA
<213> ORGANISM: murine

<400> SEQUENCE: 12
ctgttggtgg gtggagagtt                                              20

<210> SEQ ID NO 13
<211> LENGTH: 20
<212> TYPE: DNA
<213> ORGANISM: murine

<400> SEQUENCE: 13
gctgggtacc atgccttcta                                              20

<210> SEQ ID NO 14
<211> LENGTH: 20
<212> TYPE: DNA
<213> ORGANISM: murine

<400> SEQUENCE: 14
ccacacaggg tgtgatgaag                                              20

<210> SEQ ID NO 15
<211> LENGTH: 20
<212> TYPE: DNA
<213> ORGANISM: murine

<400> SEQUENCE: 15
caagagagac agggccaaag                                              20

<210> SEQ ID NO 16
<211> LENGTH: 20
<212> TYPE: DNA
<213> ORGANISM: murine

<400> SEQUENCE: 16
aaggcagcga gatacaggaa                                              20
```